(12) United States Patent
Romoda et al.

(10) Patent No.: US 10,952,898 B2
(45) Date of Patent: Mar. 23, 2021

(54) INTRAOCULAR SHUNT INSERTER

(71) Applicant: AqueSys, Inc., Parsippany, NJ (US)

(72) Inventors: Laszlo O. Romoda, San Clemente, CA (US); Christopher Horvath, Mission Viejo, CA (US)

(73) Assignee: AQUESYS, INC., Parsippany, NJ (US)

( * ) Notice: Subject to any disclaimer, the term of this patent is extended or adjusted under 35 U.S.C. 154(b) by 410 days.

(21) Appl. No.: 15/917,542

(22) Filed: Mar. 9, 2018

(65) Prior Publication Data

US 2019/0274882 A1    Sep. 12, 2019

(51) Int. Cl.
    *A61F 9/007*    (2006.01)

(52) U.S. Cl.
    CPC ................ *A61F 9/00781* (2013.01)

(58) Field of Classification Search
    CPC ............. A61M 25/01; A61M 25/0102; A61M 25/0105; A61M 25/0133; A61M 25/0152; A61B 5/15128; A61B 5/1513; A61B 5/15132; A61B 2018/00946; B26B 5/003; H01H 1/36; H01H 3/40; H01H 3/50
    See application file for complete search history.

(56) References Cited

U.S. PATENT DOCUMENTS

| | | |
|---|---|---|
| 3,654,932 A | 4/1972 | Newkirk |
| 3,788,327 A | 1/1974 | Donowitz et al. |
| 3,960,150 A | 6/1976 | Hussain et al. |
| 4,090,530 A | 5/1978 | Lange |
| 4,402,308 A | 9/1983 | Scott |
| 4,562,463 A | 12/1985 | Lipton |
| 4,583,117 A | 4/1986 | Lipton et al. |
| 4,613,329 A | 9/1986 | Bodicky |
| 4,700,692 A | 10/1987 | Baumgartner |
| 4,722,724 A | 2/1988 | Schocket |

(Continued)

FOREIGN PATENT DOCUMENTS

| | | |
|---|---|---|
| CN | 1909859 | 2/2007 |
| CN | 102170840 | 8/2011 |

(Continued)

OTHER PUBLICATIONS

Coran, (editor in chief), "Pediatric Surgery," Elsevier Saunders, published Feb. 14, 2012, 7th Edition, vol. 1, Chapter 128, pp. 1673-1697.

(Continued)

*Primary Examiner* — Adam Marcetich
(74) *Attorney, Agent, or Firm* — Nathan S. Smith; Sujohn Das; Morgan, Lewis & Bockius LLP

(57) ABSTRACT

An inserter can include a housing and a slider component. The housing can include a distal portion, a proximal portion, a longitudinal axis extending between the distal and proximal portions, an interior cavity, and an elongate slot extending along an outer surface of the housing into the cavity. The slider component can be coupled to the housing and positioned along the outer surface thereof. The slider component can be slidable along the elongate slot. The slider includes a guide tab disposed within the guide channel of the housing body. The slider further includes a friction tab having a biasing member configured to urge against the housing body to urge the guide tab against the channel wall of the guide channel.

25 Claims, 14 Drawing Sheets

(56) References Cited

U.S. PATENT DOCUMENTS

| | | | |
|---|---|---|---|
| 4,730,613 A | 3/1988 | Gordy | |
| 4,744,362 A | 5/1988 | Grundler | |
| 4,750,901 A | 6/1988 | Molteno | |
| 4,787,885 A | 11/1988 | Binder | |
| 4,804,382 A | 2/1989 | Turina et al. | |
| 4,820,626 A | 4/1989 | Williams et al. | |
| 4,826,478 A | 5/1989 | Schocket | |
| 4,836,201 A | 6/1989 | Patton et al. | |
| 4,848,340 A | 7/1989 | Bille et al. | |
| 4,863,457 A | 9/1989 | Lee | |
| 4,902,292 A | 2/1990 | Joseph | |
| 4,908,024 A | 3/1990 | Py | |
| 4,911,161 A | 3/1990 | Schechter | |
| 4,915,684 A | 4/1990 | MacKeen et al. | |
| 4,934,363 A | 6/1990 | Smith et al. | |
| 4,936,825 A | 6/1990 | Ungerleider | |
| 4,946,436 A | 8/1990 | Smith | |
| 4,968,296 A | 11/1990 | Ritch et al. | |
| 4,976,688 A * | 12/1990 | Rosenblum | A61M 25/0147 604/524 |
| 4,978,352 A | 12/1990 | Fedorov et al. | |
| 5,035,695 A * | 7/1991 | Weber, Jr. | A61B 18/1402 604/35 |
| 5,041,081 A | 8/1991 | Odrich | |
| 5,057,098 A | 10/1991 | Zelman | |
| 5,071,408 A | 12/1991 | Ahmed | |
| 5,092,837 A | 3/1992 | Ritch et al. | |
| 5,098,426 A | 3/1992 | Sklar et al. | |
| 5,098,443 A | 3/1992 | Parel et al. | |
| 5,162,641 A | 11/1992 | Fountain | |
| 5,167,645 A | 12/1992 | Castillo | |
| 5,178,604 A | 1/1993 | Baerveldt et al. | |
| 5,180,362 A | 1/1993 | Worst | |
| 5,201,750 A | 4/1993 | Hocherl et al. | |
| 5,207,660 A | 5/1993 | Lincoff | |
| 5,275,622 A | 1/1994 | Lazarus | |
| 5,290,295 A | 3/1994 | Querals et al. | |
| 5,300,020 A | 4/1994 | L'Esperance, Jr. | |
| 5,333,619 A | 8/1994 | Burgio | |
| 5,338,291 A | 8/1994 | Speckman et al. | |
| 5,342,370 A | 8/1994 | Simon et al. | |
| 5,351,678 A | 10/1994 | Clayton | |
| 5,360,339 A | 11/1994 | Rosenberg | |
| 5,368,015 A | 11/1994 | Wilk | |
| 5,370,607 A | 12/1994 | Memmen | |
| 5,399,951 A | 3/1995 | Lavallee et al. | |
| 5,410,638 A | 4/1995 | Colgate et al. | |
| 5,441,483 A * | 8/1995 | Avitall | A61B 18/1492 604/95.05 |
| 5,443,505 A | 8/1995 | Wong et al. | |
| 5,472,439 A | 12/1995 | Hurd | |
| 5,476,445 A | 12/1995 | Baerveldt et al. | |
| 5,516,522 A | 5/1996 | Peyman et al. | |
| 5,520,631 A | 5/1996 | Nordquist et al. | |
| 5,558,629 A | 9/1996 | Baerveldt et al. | |
| 5,558,630 A | 9/1996 | Fisher | |
| 5,601,094 A | 2/1997 | Reiss | |
| 5,656,026 A | 8/1997 | Joseph | |
| 5,665,093 A | 9/1997 | Atkins et al. | |
| 5,665,114 A | 9/1997 | Weadock et al. | |
| 5,670,161 A | 9/1997 | Healy et al. | |
| 5,688,562 A | 11/1997 | Hsiung | |
| 5,695,474 A | 12/1997 | Daugherty | |
| 5,704,907 A | 1/1998 | Nordquist et al. | |
| 5,707,376 A | 1/1998 | Kavteladze et al. | |
| 5,722,948 A | 3/1998 | Gross | |
| 5,763,491 A | 6/1998 | Brandt et al. | |
| 5,868,697 A | 2/1999 | Richter et al. | |
| 5,868,771 A * | 2/1999 | Herbert | A61B 17/3213 30/162 |
| 5,908,449 A | 6/1999 | Bruchman et al. | |
| 5,932,299 A | 8/1999 | Katoot | |
| 5,938,583 A | 8/1999 | Grimm | |
| 5,964,747 A | 10/1999 | Eaton et al. | |
| 6,007,511 A | 12/1999 | Prywes | |
| 6,007,578 A | 12/1999 | Schachar | |
| 6,050,970 A | 4/2000 | Baerveldt | |
| 6,086,543 A | 7/2000 | Anderson et al. | |
| 6,102,045 A | 8/2000 | Nordquist et al. | |
| 6,146,366 A | 11/2000 | Schachar | |
| 6,159,218 A | 12/2000 | Aramant et al. | |
| 6,165,210 A | 12/2000 | Lau et al. | |
| 6,203,513 B1 | 3/2001 | Yaron et al. | |
| 6,228,023 B1 | 5/2001 | Zaslaysky et al. | |
| 6,228,873 B1 | 5/2001 | Brandt et al. | |
| 6,231,546 B1 | 5/2001 | Milo | |
| 6,261,256 B1 | 7/2001 | Ahmed | |
| 6,264,665 B1 | 7/2001 | Yu et al. | |
| 6,280,468 B1 | 8/2001 | Schachar | |
| 6,413,540 B1 | 7/2002 | Yaacobi | |
| 6,450,937 B1 | 9/2002 | Mercereau et al. | |
| 6,464,698 B1 * | 10/2002 | Falwell | A61B 18/1492 606/41 |
| 6,471,666 B1 | 10/2002 | Odrich | |
| 6,483,930 B1 | 11/2002 | Musgrave et al. | |
| 6,514,238 B1 | 2/2003 | Hughes | |
| 6,524,275 B1 | 2/2003 | Lynch et al. | |
| 6,533,768 B1 | 3/2003 | Hill | |
| 6,544,249 B1 | 4/2003 | Yu et al. | |
| 6,558,342 B1 | 5/2003 | Yaron et al. | |
| 6,595,945 B2 | 7/2003 | Brown | |
| 6,638,239 B1 | 10/2003 | Bergheim et al. | |
| 6,699,210 B2 | 3/2004 | Williams et al. | |
| 6,726,664 B2 | 4/2004 | Yaron et al. | |
| D490,152 S | 5/2004 | Myall et al. | |
| 6,736,791 B1 | 5/2004 | Tu et al. | |
| 6,752,753 B1 | 6/2004 | Hoskins et al. | |
| 6,881,198 B2 | 4/2005 | Brown | |
| 6,936,053 B1 | 8/2005 | Weiss | |
| 6,939,298 B2 | 9/2005 | Brown et al. | |
| 7,008,396 B1 | 3/2006 | Straub | |
| 7,037,335 B2 | 5/2006 | Freeman et al. | |
| 7,041,077 B2 | 5/2006 | Shields | |
| 7,094,225 B2 | 8/2006 | Tu et al. | |
| 7,118,547 B2 | 10/2006 | Dahan | |
| 7,135,009 B2 | 11/2006 | Tu et al. | |
| 7,163,543 B2 | 1/2007 | Smedley et al. | |
| 7,186,232 B1 | 3/2007 | Smedley et al. | |
| 7,207,980 B2 | 4/2007 | Christian et al. | |
| 7,291,125 B2 | 11/2007 | Coroneo | |
| 7,331,984 B2 | 2/2008 | Tu et al. | |
| 7,431,709 B2 | 10/2008 | Pinchuk et al. | |
| 7,431,710 B2 | 10/2008 | Tu et al. | |
| 7,458,953 B2 | 12/2008 | Peyman | |
| 7,488,303 B1 | 2/2009 | Haffner et al. | |
| 7,594,899 B2 | 9/2009 | Pinchuk et al. | |
| 7,625,384 B2 | 12/2009 | Eriksson et al. | |
| 7,658,729 B2 | 2/2010 | Hull | |
| 7,708,711 B2 | 5/2010 | Tu et al. | |
| 7,722,549 B2 | 5/2010 | Nakao | |
| 7,837,644 B2 | 11/2010 | Pinchuk et al. | |
| 7,867,186 B2 | 1/2011 | Haffner et al. | |
| 7,892,282 B2 | 2/2011 | Shepherd | |
| 8,109,896 B2 | 2/2012 | Nissan et al. | |
| 8,267,882 B2 | 9/2012 | Euteneuer et al. | |
| 8,277,437 B2 | 10/2012 | Saal et al. | |
| 8,308,701 B2 | 11/2012 | Horvath et al. | |
| 8,337,393 B2 | 12/2012 | Silverstrini et al. | |
| 8,337,509 B2 | 12/2012 | Schieber et al. | |
| 8,377,122 B2 | 2/2013 | Silvestrini et al. | |
| 8,425,449 B2 | 4/2013 | Wardle et al. | |
| 8,444,589 B2 | 5/2013 | Silvestrini | |
| 8,486,000 B2 | 7/2013 | Coroneo | |
| 8,506,515 B2 | 8/2013 | Burns et al. | |
| 8,512,404 B2 | 8/2013 | Frion et al. | |
| 8,529,492 B2 | 9/2013 | Clauson et al. | |
| 8,535,333 B2 | 9/2013 | de Juan, Jr. et al. | |
| 8,545,430 B2 | 10/2013 | Silvestrini | |
| 8,585,629 B2 | 11/2013 | Grabner et al. | |
| 8,597,301 B2 | 12/2013 | Mitchell | |
| 8,608,632 B1 | 12/2013 | Brigatti et al. | |
| 8,663,303 B2 | 3/2014 | Horvath et al. | |
| 8,721,702 B2 | 5/2014 | Romoda et al. | |
| 8,758,290 B2 | 6/2014 | Horvath et al. | |

(56) References Cited

U.S. PATENT DOCUMENTS

| | | |
|---|---|---|
| 8,765,210 B2 | 7/2014 | Romoda et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,974,511 B2 | 3/2015 | Horvath et al. |
| 9,017,276 B2 | 4/2015 | Horvath et al. |
| 9,044,301 B1 | 6/2015 | Pinchuk et al. |
| 9,095,411 B2 | 8/2015 | Horvath et al. |
| 9,095,413 B2 | 8/2015 | Romoda et al. |
| 9,192,516 B2 | 11/2015 | Horvath et al. |
| 9,271,869 B2 | 3/2016 | Horvath et al. |
| 9,283,116 B2 | 3/2016 | Romoda et al. |
| 9,326,891 B2 | 5/2016 | Horvath et al. |
| 9,393,153 B2 | 7/2016 | Horvath |
| 2001/0025150 A1 | 9/2001 | de Juan et al. |
| 2001/0056254 A1 | 12/2001 | Cragg et al. |
| 2002/0087149 A1 | 7/2002 | McCary |
| 2002/0099434 A1 | 7/2002 | Buscemi et al. |
| 2002/0133168 A1 | 9/2002 | Smedley et al. |
| 2003/0015203 A1 | 1/2003 | Makower |
| 2003/0050574 A1 | 3/2003 | Krueger |
| 2003/0060752 A1 | 3/2003 | Bergheim et al. |
| 2003/0093084 A1 | 5/2003 | Nissan et al. |
| 2003/0097053 A1 | 5/2003 | Itoh |
| 2003/0187383 A1 | 10/2003 | Weber et al. |
| 2003/0236483 A1 | 12/2003 | Ren |
| 2003/0236484 A1 | 12/2003 | Lynch et al. |
| 2004/0077987 A1 | 4/2004 | Rapacki et al. |
| 2004/0147870 A1 | 7/2004 | Burns et al. |
| 2004/0158269 A1* | 8/2004 | Holman .............. A61B 17/3217 606/167 |
| 2004/0199130 A1 | 10/2004 | Chornenky et al. |
| 2004/0210209 A1 | 10/2004 | Yeung et al. |
| 2004/0215133 A1 | 10/2004 | Weber et al. |
| 2004/0216749 A1 | 11/2004 | Tu |
| 2004/0236343 A1 | 11/2004 | Taylor et al. |
| 2004/0254521 A1 | 12/2004 | Simon |
| 2004/0260227 A1 | 12/2004 | Lisk et al. |
| 2005/0049578 A1 | 3/2005 | Tu et al. |
| 2005/0101967 A1 | 5/2005 | Weber et al. |
| 2005/0143363 A1 | 6/2005 | De Juan et al. |
| 2005/0177183 A1* | 8/2005 | Thorne ................. A61B 17/32 606/167 |
| 2005/0246023 A1 | 11/2005 | Yeung |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0052721 A1 | 3/2006 | Dunker et al. |
| 2006/0064112 A1 | 3/2006 | Perez |
| 2006/0106370 A1 | 5/2006 | Baerveldt et al. |
| 2006/0116625 A1 | 6/2006 | Renati et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0173446 A1 | 8/2006 | Dacquay et al. |
| 2006/0200113 A1 | 9/2006 | Haffner et al. |
| 2006/0241411 A1 | 10/2006 | Field et al. |
| 2007/0027537 A1 | 2/2007 | Castillejos |
| 2007/0093783 A1 | 4/2007 | Kugler et al. |
| 2007/0118065 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1 | 8/2007 | De Juan et al. |
| 2007/0202186 A1 | 8/2007 | Yamamoto |
| 2007/0263172 A1 | 11/2007 | Mura |
| 2007/0293872 A1 | 12/2007 | Peyman |
| 2008/0015633 A1 | 1/2008 | Abbott et al. |
| 2008/0057106 A1 | 3/2008 | Erickson et al. |
| 2008/0108933 A1 | 5/2008 | Yu et al. |
| 2008/0147001 A1 | 6/2008 | Al-Marashi et al. |
| 2008/0181929 A1 | 7/2008 | Robinson et al. |
| 2008/0249467 A1 | 10/2008 | Burnett et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0124973 A1 | 5/2009 | D'Agostino et al. |
| 2009/0182421 A1 | 7/2009 | Silvestrini et al. |
| 2009/0209910 A1 | 8/2009 | Kugler et al. |
| 2009/0216106 A1 | 8/2009 | Takii |
| 2009/0264813 A1 | 10/2009 | Chang |
| 2009/0270890 A1 | 10/2009 | Robinson et al. |
| 2009/0281520 A1 | 11/2009 | Highley et al. |
| 2009/0287136 A1 | 11/2009 | Castillejos |
| 2010/0004581 A1 | 1/2010 | Brigatti et al. |
| 2010/0063478 A1 | 3/2010 | Selkee |
| 2010/0063512 A1 | 3/2010 | Braga |
| 2010/0098772 A1 | 4/2010 | Robinson et al. |
| 2010/0100104 A1 | 4/2010 | Yu et al. |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0173866 A1 | 7/2010 | Hee et al. |
| 2010/0191103 A1 | 7/2010 | Stamper et al. |
| 2010/0191224 A1 | 7/2010 | Butcher |
| 2010/0249691 A1 | 9/2010 | Van Der Mooren et al. |
| 2010/0328606 A1 | 12/2010 | Peyman |
| 2011/0009874 A1 | 1/2011 | Wardle et al. |
| 2011/0046536 A1 | 2/2011 | Stegmann et al. |
| 2011/0098627 A1 | 4/2011 | Wilcox |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2011/0275958 A1* | 11/2011 | Barrett ............... A61B 17/1721 600/595 |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123434 A1 | 5/2012 | Grabner et al. |
| 2012/0165720 A1 | 6/2012 | Horvath et al. |
| 2012/0165933 A1 | 6/2012 | Haffner et al. |
| 2012/0197175 A1 | 8/2012 | Horvath et al. |
| 2012/0215241 A1* | 8/2012 | Trees .................... A61F 9/0133 606/167 |
| 2012/0226150 A1 | 9/2012 | Balicki et al. |
| 2012/0310137 A1 | 12/2012 | Silvestrini |
| 2013/0158462 A1 | 6/2013 | Wardle et al. |
| 2013/0158574 A1* | 6/2013 | Yi ...................... A61B 17/3213 606/167 |
| 2013/0184631 A1 | 7/2013 | Pinchuk |
| 2013/0211314 A1 | 8/2013 | Boey et al. |
| 2013/0237958 A1 | 9/2013 | Arrigo |
| 2013/0245573 A1 | 9/2013 | de Juan, Jr. et al. |
| 2013/0253528 A1 | 9/2013 | Haffner et al. |
| 2013/0281817 A1 | 10/2013 | Schaller et al. |
| 2013/0281908 A1 | 10/2013 | Schaller et al. |
| 2013/0345515 A1 | 12/2013 | Fitzmaaurice |
| 2014/0066833 A1 | 3/2014 | Yaron et al. |
| 2014/0081195 A1 | 3/2014 | Clauson et al. |
| 2014/0135916 A1 | 5/2014 | Clauson et al. |
| 2014/0213958 A1 | 7/2014 | Clauson et al. |
| 2014/0236066 A1 | 8/2014 | Horvath et al. |
| 2014/0243730 A1 | 8/2014 | Horvath |
| 2014/0275923 A1 | 9/2014 | Haffner et al. |
| 2014/0276332 A1 | 9/2014 | Crimaldi et al. |
| 2014/0277349 A1 | 9/2014 | Vad |
| 2014/0303544 A1 | 10/2014 | Haffner et al. |
| 2014/0323995 A1 | 10/2014 | Clauson et al. |
| 2014/0343476 A1 | 11/2014 | Penhasi |
| 2014/0371651 A1 | 12/2014 | Pinchuk |
| 2015/0005689 A1 | 1/2015 | Horvath et al. |
| 2015/0011926 A1 | 1/2015 | Reitsamer et al. |
| 2015/0027866 A1* | 1/2015 | Morimoto ................ H01H 1/36 200/11 R |
| 2015/0038893 A1 | 2/2015 | Haffner et al. |
| 2015/0133946 A1 | 5/2015 | Horvath et al. |
| 2015/0238687 A1 | 8/2015 | Novakovic et al. |
| 2015/0265469 A1 | 9/2015 | Bhandari et al. |

(56) References Cited

U.S. PATENT DOCUMENTS

| | | |
|---|---|---|
| 2015/0290035 A1 | 10/2015 | Horvath et al. |
| 2015/0374545 A1 | 12/2015 | Horvath et al. |
| 2016/0135993 A1 | 5/2016 | Horvath et al. |
| 2016/0135994 A1 | 5/2016 | Romoda et al. |
| 2016/0158063 A1 | 6/2016 | Romoda et al. |
| 2016/0249947 A1* | 9/2016 | Castanon ............ A61B 17/3213 606/167 |
| 2016/0250071 A1 | 9/2016 | Horvath et al. |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0256323 A1 | 9/2016 | Horvath et al. |
| 2016/0278982 A1 | 9/2016 | Horvath et al. |
| 2016/0354244 A1 | 12/2016 | Horvath et al. |
| 2016/0354245 A1 | 12/2016 | Horvath et al. |
| 2017/0066578 A1* | 3/2017 | Kierstead ............ B65H 75/366 |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0340352 A1* | 11/2017 | Stone ................. A61B 10/0275 |
| 2017/0348150 A1 | 12/2017 | Horvath et al. |
| 2018/0008464 A1 | 1/2018 | Horvath et al. |
| 2018/0199797 A1 | 7/2018 | London |
| 2018/0282036 A1* | 10/2018 | Watson .............. B65D 63/1027 |
| 2019/0030285 A1 | 1/2019 | Prabhu |
| 2019/0054272 A1 | 2/2019 | Tal |
| 2019/0069770 A1 | 3/2019 | Bourget |
| 2019/0290314 A1 | 9/2019 | Gemer |
| 2019/0380704 A1* | 12/2019 | Fleischmann .......... A61B 17/08 |
| 2020/0046213 A1 | 2/2020 | Bendory |
| 2020/0054353 A1 | 2/2020 | Yun |

FOREIGN PATENT DOCUMENTS

| | | |
|---|---|---|
| GB | 2296663 | 7/1996 |
| JP | 2009-523540 | 6/2009 |
| JP | 2012-527318 | 11/2012 |
| JP | 2014-500758 | 1/2014 |
| RU | 2313315 | 12/2007 |
| WO | WO 98/23237 | 6/1998 |
| WO | WO 2000/056255 | 9/2000 |
| WO | WO 2002/74052 | 9/2002 |
| WO | WO 2007/087061 | 8/2007 |
| WO | WO 2008/005873 | 1/2008 |
| WO | WO 2010/003011 | 1/2010 |
| WO | WO 2011/155922 | 12/2011 |
| WO | WO 2014/150292 | 9/2014 |
| WO | WO 2016/159999 | 10/2016 |
| WO | WO 2017/184881 | 10/2017 |

OTHER PUBLICATIONS

Quere, "Fluid Coating on a Fiber," Annu. Rev. Fluid Mech. 1999, 31:347-84.

Horvath, U.S. Appl. No. 15/703,503, "Manually Adjustable Intraocular Flow Regulation," filed Nov. 8, 2017.

* cited by examiner

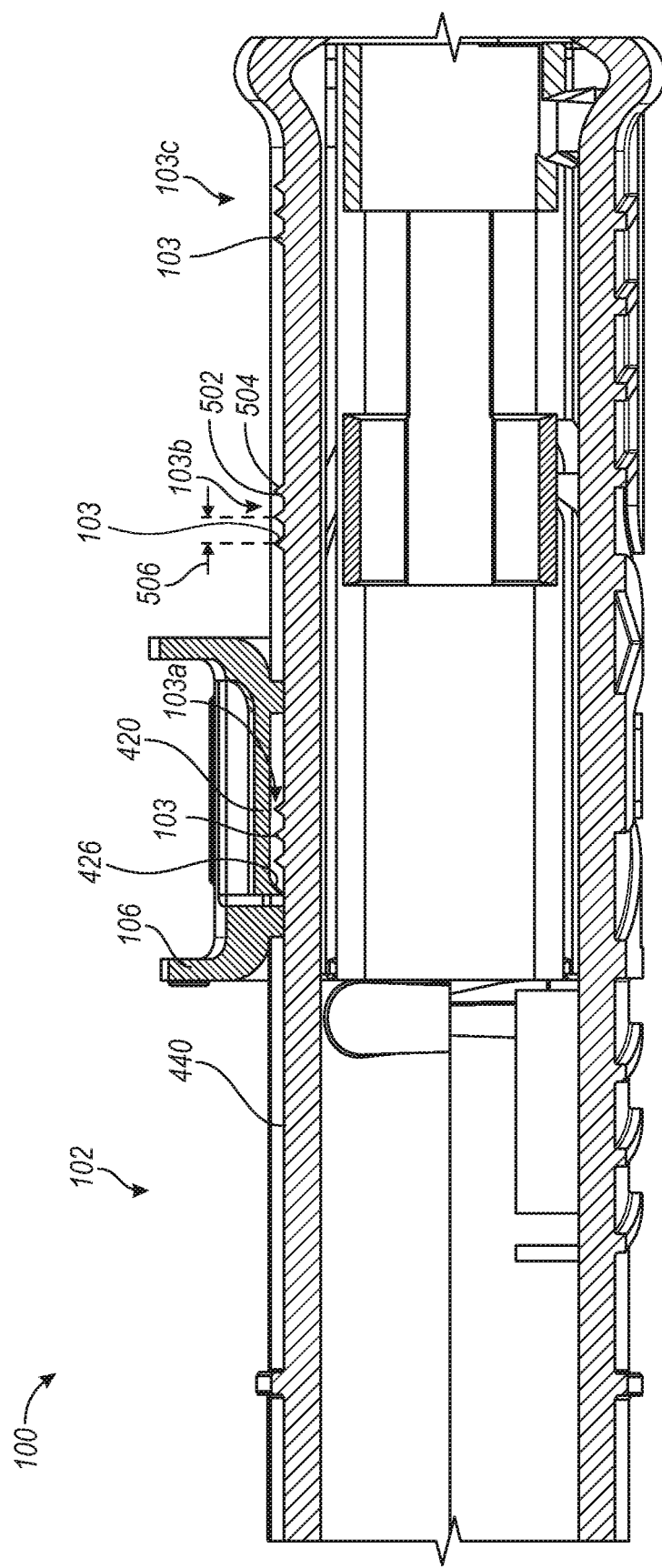

INTRAOCULAR SHUNT INSERTER

BACKGROUND

Glaucoma is a disease of the eye that affects millions of people. Glaucoma is associated with an increase in intraocular pressure resulting either from a failure of a drainage system of an eye to adequately remove aqueous humor from an anterior chamber of the eye or overproduction of aqueous humor by a ciliary body in the eye. Build-up of aqueous humor and resulting intraocular pressure may result in irreversible damage to the optic nerve and the retina, which may lead to irreversible retinal damage and blindness.

Glaucoma may be treated in a number of different ways. One manner of treatment involves delivery of drugs such as beta-blockers or prostaglandins to the eye to either reduce production of aqueous humor or increase flow of aqueous humor from an anterior chamber of the eye. Glaucoma filtration surgery is a surgical procedure typically used to treat glaucoma. The procedure involves placing a shunt in the eye to relieve intraocular pressure by creating a pathway for draining aqueous humor from the anterior chamber of the eye. The shunt is typically positioned in the eye such that it creates a drainage pathway between the anterior chamber of the eye and a region of lower pressure. Such fluid flow pathways allow for aqueous humor to exit the anterior chamber.

SUMMARY

The importance of lowering intraocular pressure (IOP) in delaying glaucomatous progression is well documented. When drug therapy fails, or is not tolerated, surgical intervention is warranted. There are various surgical filtration methods for lowering intraocular pressure by creating a fluid flow-path between the anterior chamber and the subconjunctival tissue. In one particular method, an intraocular shunt is implanted with an inserter by directing a needle, which holds the shunt through the cornea, across the anterior chamber, and through the trabecular meshwork and sclera, and into the subconjunctival space. See, for example, U.S. Pat. No. 6,544,249, U.S. Patent Application Publication No. 2008/0108933, and U.S. Pat. No. 6,007,511, the entireties of which are incorporated herein by reference.

Existing inserters may have components that move inadvertently and may not always provide desired levels of precision and feedback during a procedure. During a procedure, an operator may not be able to differentiate between the different stages of the insertion process, such as shunt insertion and needle retraction. This may require the operator to manually and/or visually review steps of the procedure, which increases the time that a careful and attentive operator must devote to each step of the procedure. As such, this can increase surgery time, potentially cause greater trauma to the patient, and nevertheless be reliant on tactile or visual perception of components without certainty that certain milestones or positions have been achieved.

Accordingly, the present disclosure contemplates these problems, provides solutions to these problems, and relates to the realization that precision can be increased while reducing operator effort and surgery time, in some embodiments, implementing certain advantageous features in a shunt inserter.

Some embodiments disclosed herein provide an intraocular shunt inserter having an actuator that that permits the operator to deliver and/or release an intraocular shunt. The inserter can be configured to provide a frictional track or resistance against which an operator can move the actuator, whether sliding or rotating. This resistance to movement can ensure that the inserter exposes or releases the shunt only when intended by the operator. Further, the resistance can tend to cause the operator to operate the inserter using a greater degree of precision and control.

Optionally, some embodiments can comprise one or more feedback components that can serve as indicators of motion or completion of steps in the procedure. For example, the inserter can comprise an actuator, whether sliding or rotating, that can provide one or more audible clicks and/or barriers of increased resistance that can serve as signals to the operator that a certain position or step of the procedure has been completed. In some embodiments, a slider component can contact against a first engagement structure or indicator on the inserter to create an audible click or barrier of increased resistance. Continued movement beyond the click or barrier of increased resistance can allow the operator to move the slider component towards a second, third, fourth, or other engagement structure or indicator that can create an audible click or barrier of increased resistance to signal to the operator that the slider component has been advanced to a predetermined location and/or that additional positions or steps of the procedure have been completed. Accordingly, the inserter can advantageously provide improved precision and feedback to an operator.

Further, some embodiments disclosed herein can optionally provide an inserter with a bended shaft or needle that can provide greater tactile control of the inserter and improved clearance during a procedure. The needle can extend from a distal end portion of the inserter and comprise a bend at which a longitudinal axis of the needle is redirected along a different axis. The bend can enable an operator to more easily manipulate and/or perceive the position of a bevel of the needle during the procedure. Thus, some embodiments can advantageously permit an operator to more easily visually verify that a certain result has been achieved. For example, by rotating the bevel of the needle, an operator can "tent" the conjunctiva of the eye, thereby facilitating placement and delivery of the intraocular shunt into a subconjunctival target location. Further, the bend can cause a longitudinal axis of a housing of the inserter to be spaced at a greater distance apart from a patient's face during the procedure than compared to straight-needle-type inserters.

For example, an inserter can include a housing and a slider component. The housing include a distal portion, a proximal portion, a longitudinal axis extending between the distal and proximal portions, an interior cavity, and an elongate slot extending along an outer surface of the housing into the cavity. The slider component can be coupled to the housing and positioned along the outer surface of the housing. The slider component can be slidable along the elongate slot to operate the inserter. The slider component can include a guide tab disposed within the guide channel of the housing body. The slider component can also include a friction tab with a biasing member configured to urge against the housing body to urge the guide tab against the channel wall of the guide channel.

An operator can operate the inserter by urging the slider component along an axis of the inserter. The slider component can actuate a deployment mechanism of the inserter to deliver and release an intraocular shunt. In order to do so, the operator must overcome an initial friction force provided by a friction tab of the slider component against the housing.

The operator can use the slider component to advance a plunger of the inserter to urge the shunt within a lumen of the needle.

During operation of the inserter, an operator can receive tactile or horrible feedback from engagement structures of the housing, for example, as the friction tab moves across an engagement structure. The feedback can correspond to the position of the shunt relative to the needle within the inserter. The feedback can be provided by a discontinuity on the housing.

For example, in some embodiments, the inserter can generate an audible signal using a biasing member configured to engage a discontinuity of the housing body. The audible or tactile signal can indicate a position of the slider component relative to the inserter and/or indicate a position of the shunt or stage of shunt delivery.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIGS. 6A-6C are cross-sectional views of engagement structures of the inserter, according to some embodiments.

DETAILED DESCRIPTION

Figure 1A:
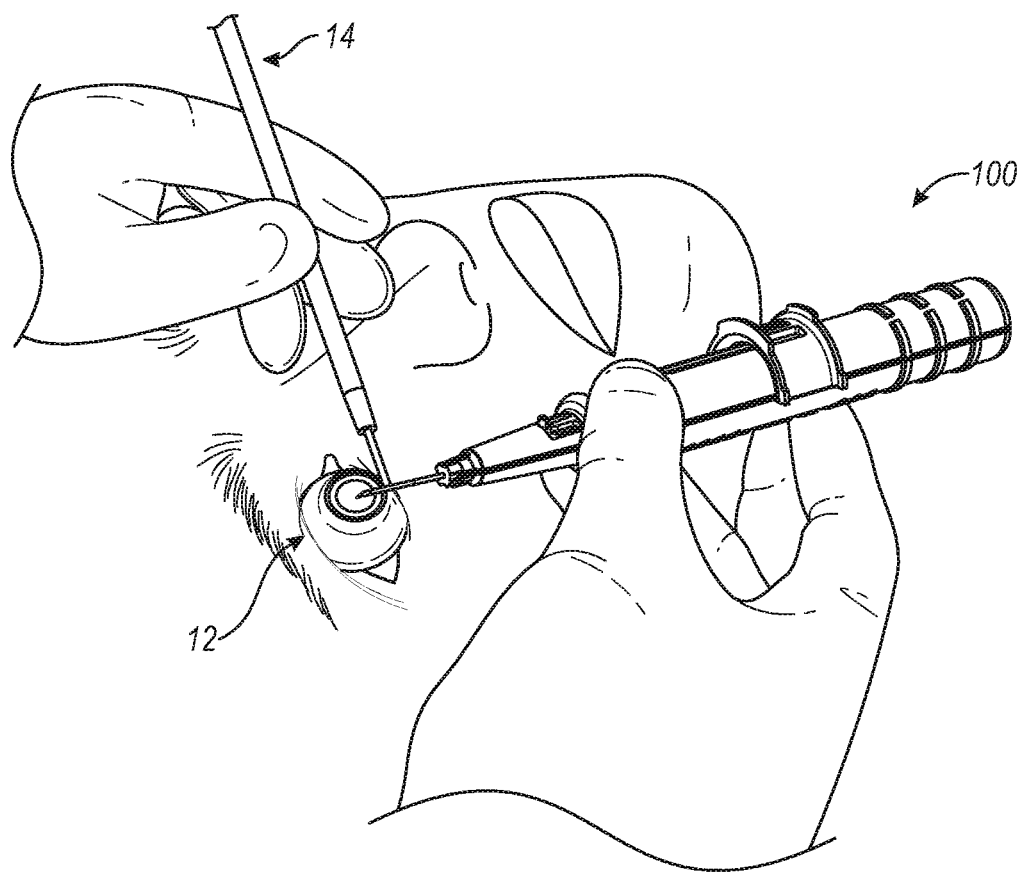
FIG. 1A is a schematic view of a procedure for implanting an intraocular shunt into an eye using an inserter, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Glaucoma is a disease in which the optic nerve is damaged, leading to progressive, irreversible loss of vision. It is typically associated with increased pressure of the fluid (i.e., aqueous humor) in the eye. Untreated glaucoma leads to permanent damage of the optic nerve and resultant visual field loss, which can progress to blindness. Once lost, this damaged visual field cannot be recovered.

In conditions of glaucoma, the pressure of the aqueous humor in the eye (anterior chamber) increases and this resultant increase of pressure can cause damage to the vascular system at the back of the eye and especially to the optic nerve. The treatment of glaucoma and other diseases that lead to elevated pressure in the anterior chamber involves relieving pressure within the anterior chamber to a normal level.9

Glaucoma filtration surgery is a surgical procedure typically used to treat glaucoma. The procedure involves placing a shunt in the eye to relieve intraocular pressure by creating a pathway for draining aqueous humor from the anterior chamber of the eye. The shunt is typically positioned in the eye such that it creates a drainage pathway between the anterior chamber of the eye and a region of lower pressure. Various structures and/or regions of the eye having lower pressure that have been targeted for aqueous humor drainage include Schlemm's canal, the subconjunctival space, the episcleral vein, the suprachoroidal space, the intra-Tenon's adhesion space, and the subarachnoid space. Shunts may be implanted using an ab externo approach (e.g., entering through the conjunctiva and inwards through the sclera) or an ab interno approach (e.g., entering through the cornea, across the anterior chamber, through the trabecular meshwork and sclera). For example, ab interno approaches for implanting an intraocular shunt in the subconjunctival space are shown for example in Yu et al. (U.S. Pat. No. 6,544,249 and U.S. Patent Application Publication No. 2008/0108933) and Prywes (U.S. Pat. No. 6,007,511), the contents of each of which are incorporated by reference herein in its entirety.

Some methods can involve inserting into the eye a hollow shaft configured to hold an intraocular shunt. In some embodiments, the hollow shaft can be a component of a deployment device that may deploy the intraocular shunt. The hollow shaft can be coupled to a deployment device or be part of the deployment device itself. The deployment devices can include devices such as those as described in co-owned U.S. Pat. Nos. 9,585,790, 8,721,792, 8,852,136, and U.S. Patent Application Publication No. 2012/0123434, filed on Nov. 15, 2010, the contents of each of which are incorporated by reference herein in their entireties.

As noted above, conventional deployment devices or inserters may not provide desired levels of precision and feedback, requiring additional operator effort and surgical time. The present disclosure provides various embodiments of methods and devices that can enable an operator to implant a shunt using an inserter with improved comfort, feedback and precision while reducing surgical time. As used herein, the term "shunt" includes hollow microfistula tubes similar to the type generally described in U.S. Pat. No.

6,544,249 as well as other structures that include one or more lumens or other flow paths therethrough.

In accordance with some embodiments, the inserter can be advanced into the eye via an ab-interno or an ab-externo approach. Thereafter, the shunt can be deployed from the shaft into the eye such that the shunt forms a passage from the anterior chamber into an area of lower pressure, such as Schlemm's canal, the subconjunctival space, the episcleral vein, the suprachoroidal space, the intra-Tenon's adhesion space, the subarachnoid space, or other areas of the eye. The hollow shaft is then withdrawn from the eye. Methods for delivering and implanting bioabsorbable or permanent tubes or shunts, as well as implantation devices for performing such methods, are generally disclosed in applicant's applications, including U.S. Patent Application Publication Nos. 2012/0197175, 2015/0011926, and 2016/0354244, U.S. patent application Ser. No. 15/613,018, as well as in U.S. Pat. Nos. 6,007,511, 6,544,249, 8,852,136, and 9,585,790 each of which are incorporated by reference in their entireties.

Some methods can be conducted by making an incision in the eye prior to insertion of the deployment device. However, in some instances, the method may be conducted without making an incision in the eye prior to insertion of the deployment device. In some embodiments, the shaft that is connected to the deployment device has a sharpened point or tip. In some embodiments, the hollow shaft is a needle. Exemplary needles that may be used are commercially available from Terumo Medical Corp. (Elkington, Md.). In some embodiments, the needle can have a hollow interior and a beveled tip, and the intraocular shunt can be held within the hollow interior of the needle. In some embodiments, the needle can have a hollow interior and a triple ground point or tip.

Some methods can be conducted without needing to remove an anatomical portion or feature of the eye, including but not limited to the trabecular meshwork, the iris, the cornea, or aqueous humor. Some methods can be conducted without inducing substantial ocular inflammation, such as subconjunctival blebbing or endophthalmitis. Some methods can be achieved using an ab interno approach by inserting the hollow shaft configured to hold the intraocular shunt through the cornea, across the anterior chamber, through the trabecular meshwork, and into the intra-scleral or intra-Tenon's adhesion space. However, some methods may be conducted using an ab externo approach.

In some methods conducted using an ab interno approach, the angle of entry through the cornea can be altered to affect optimal placement of the shunt in the intra-Tenon's adhesion space. The hollow shaft can be inserted into the eye at an angle above or below the corneal limbus, in contrast with entering through the corneal limbus. For example, the hollow shaft can be inserted from about 0.25 mm to about 3.0 mm above the corneal limbus. The shaft can be inserted from about 0.5 mm to about 2.5 mm above the corneal limbus. The shaft can also be inserted from about 1.0 mm to about 2.0 mm above the corneal limbus, or any specific value within any of these ranges. For example, the hollow shaft can be inserted above the corneal limbus at distances of about: 1.0 mm, 1.1 mm, 1.2 mm, 1.3 mm, 1.4 mm, 1.5 mm, 1.6 mm, 1.7 mm, 1.8 mm, 1.9 mm, or 2.0 mm.

Further, in some embodiments, placement of the shunt farther from the limbus at the exit site, as provided by an angle of entry above the limbus, can provide access to more lymphatic channels for drainage of aqueous humor, such as the episcleral lymphatic network, in addition to the conjunctival lymphatic system. A higher angle of entry also results in flatter placement in the intra-Tenon's adhesion space so that there is less bending of the shunt.

As discussed in U.S. Pat. No. 8,852,136, the entirety of which is incorporated herein by reference, in some embodiments, to ensure proper positioning and functioning of the intraocular shunt, the depth of penetration into the intra-Tenon's adhesion space may be important when performing some methods.

In some methods, the distal tip of the hollow shaft can pierce the sclera and intra-Tenon's adhesion space without coring, removing or causing major tissue distortion of the surrounding eye tissue. The shunt is then deployed from the shaft. Preferably, a distal portion of the hollow shaft (as opposed to the distal tip) completely enters the intra-Tenon's adhesion space before the shunt is deployed from the hollow shaft.

In accordance with some embodiments, the hollow shaft can comprise a flat bevel needle, such as a needle having a triple-ground point. The tip bevel can first pierce through the sclera and into the intra-Tenon's adhesion space by making a horizontal slit. In some methods, the needle can be advanced even further such that the entire flat bevel penetrates into the intra-Tenon's adhesion space, to spread and open the tissue to a full circular diameter.

Further, in accordance with an aspect of some methods, the intra-Tenon's channel can be urged open by the flat bevel portion of the needle so that the material around the opening is sufficiently stretched and a pinching of the shunt in that zone is avoided, thus preventing the shunt from failing due to the pinching or constriction. Full entry of the flat bevel into the intra-Tenon's adhesion space causes minor distortion and trauma to the local area. However, this area ultimately surrounds and conforms to the shunt once the shunt is deployed in the eye.

In some embodiments, the inserter can function as a one-handed device in order to allow an operator to keep their other hand on a fixation device that holds the eye, such as a hook. This can improve surgical control and placement accuracy and makes the surgery easier as well.

An illustration of a procedure for treating an eye 12 is shown in FIG. 1A. FIG. 1A illustrates the use of a hook 14 for holding the eye 12 and an inserter 100 for introducing an intraocular shunt into the eye.

Figure 1B:
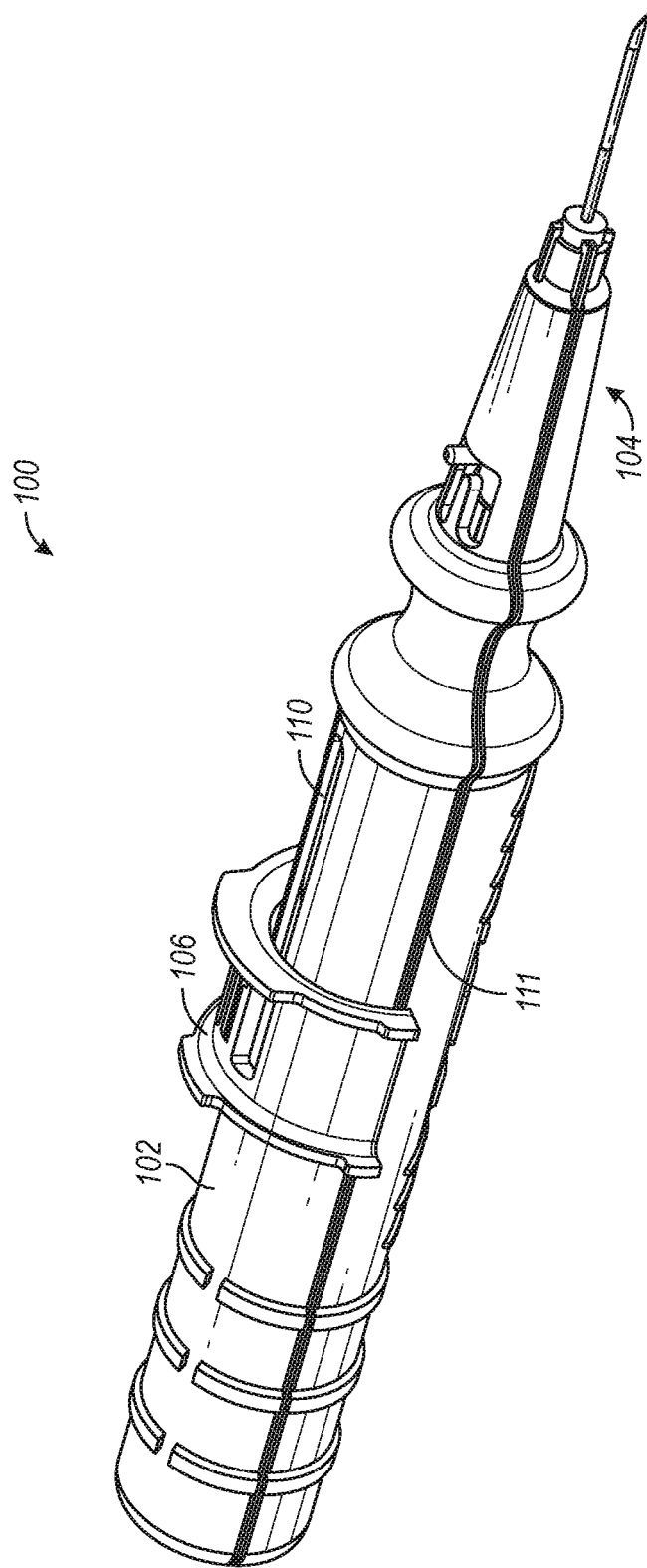
FIG. 1B is a perspective view of an inserter for implanting an intraocular shunt into an eye, according to some embodiments.

FIGS. 1B-9 illustrate further details of the inserter 100 shown in FIG. 1A. The inserter 100 can be actuated using a single hand, thus facilitating use of the inserter by an operator. The inserter 100 can comprise a housing 102, a needle assembly 104, and a slider component 106. As shown in FIG. 1B, the inserter 100 can be configured such that the slider component 106 is coupled to the housing 102 via guide channels 111 and slidable along an elongate slot 110 of the housing 102. The slider component 106 can be selectively movable by an operator in order to actuate movement of components of the needle assembly 104.

For example, when the slider component 106 moves distally along the slot 110 (i.e., in a direction toward the needle assembly 104), the slider component 106 can result in or cause a shunt (not shown) to be advanced within the needle assembly 104, and in some embodiments, released from the needle assembly 104. In accordance with some embodiments discussed further herein, movement of the slider component 106 can result in translational and/or rotational movement of components of the needle assembly 104. The sliding movement of the slider component 106 can be converted into rotational movement, which can thereafter be converted to movement along a longitudinal axis of the inserter 100. One of the benefits of this innovative and complex movement-conversion mechanism is that it enables embodiments of the inserter to provide precise, measured movements of its components within a compact assembly.

Figure 2:
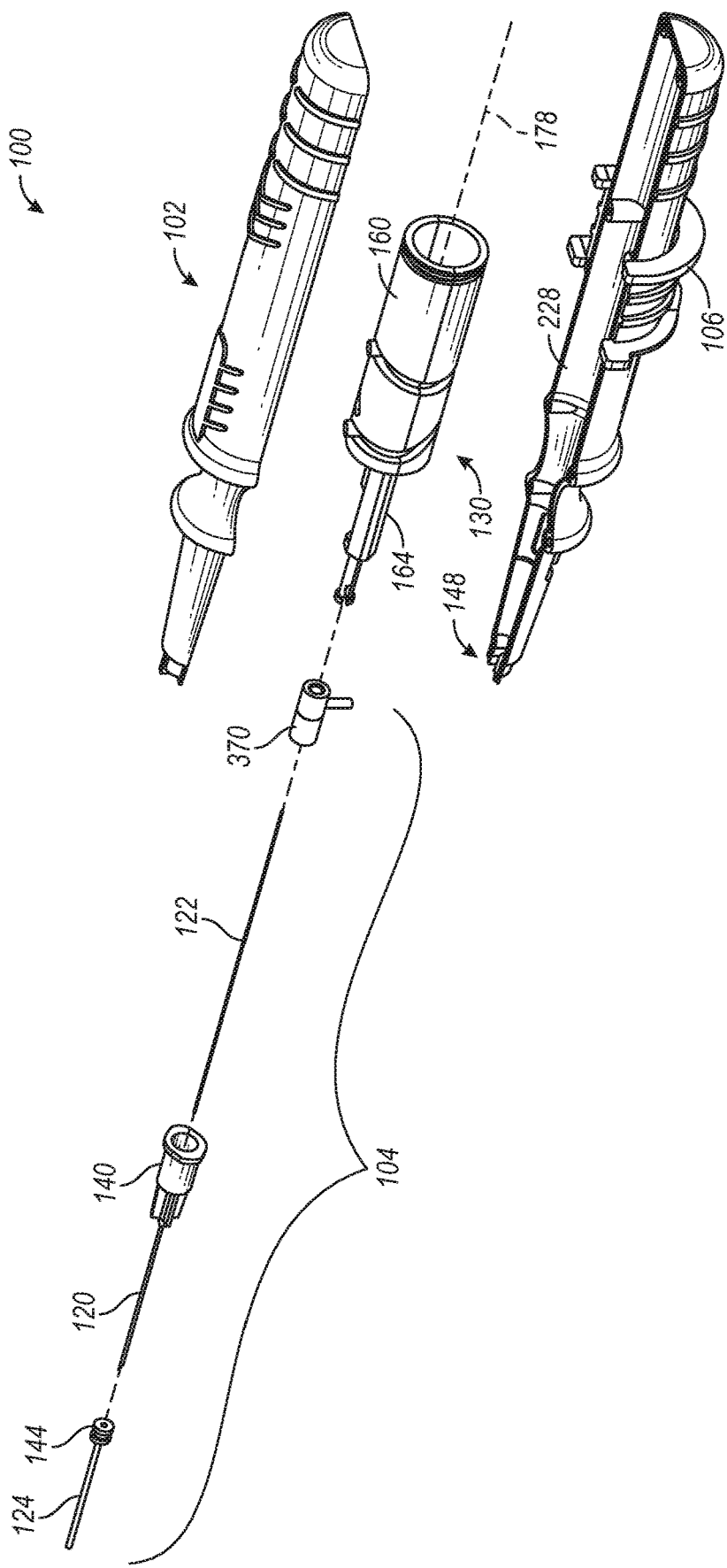
FIG. 2 is a perspective, exploded view of the inserter shown in FIG. 1B, according to some embodiments.

As illustrated in FIG. 2, the needle assembly 104 can comprise a needle component 120, a plunger 122, and a sleeve component 124. The needle component 120 can comprise a 25 GA or 27 GA needle. The plunger 122 can be slidably movable within a lumen of the needle component 120 along a longitudinal axis 178 of the inserter 100. Further, the needle component 120 can be slidably movable within a lumen of the sleeve component 124 along the longitudinal axis 178. Each of the needle component 120 and the plunger 122 can be coupled to respective drive components of a drive assembly 130 disposed within the housing 102. When in the assembled state, the inserter 100 can be configured such that the needle component 120, the plunger 122, and the sleeve component 124 are aligned along or coaxial with the longitudinal axis 178. Some drive assemblies for actuating a plunger and for withdrawing a needle of an inserter are disclosed in U.S. patent application Ser. Nos. 13/336,803, 12/946,645, 12/620,564, 12/946,653, 12/946,565, and 11/771,805 and U.S. Pat. No. 9,585,790, the entireties of which are incorporated herein by reference.

Figure 3:
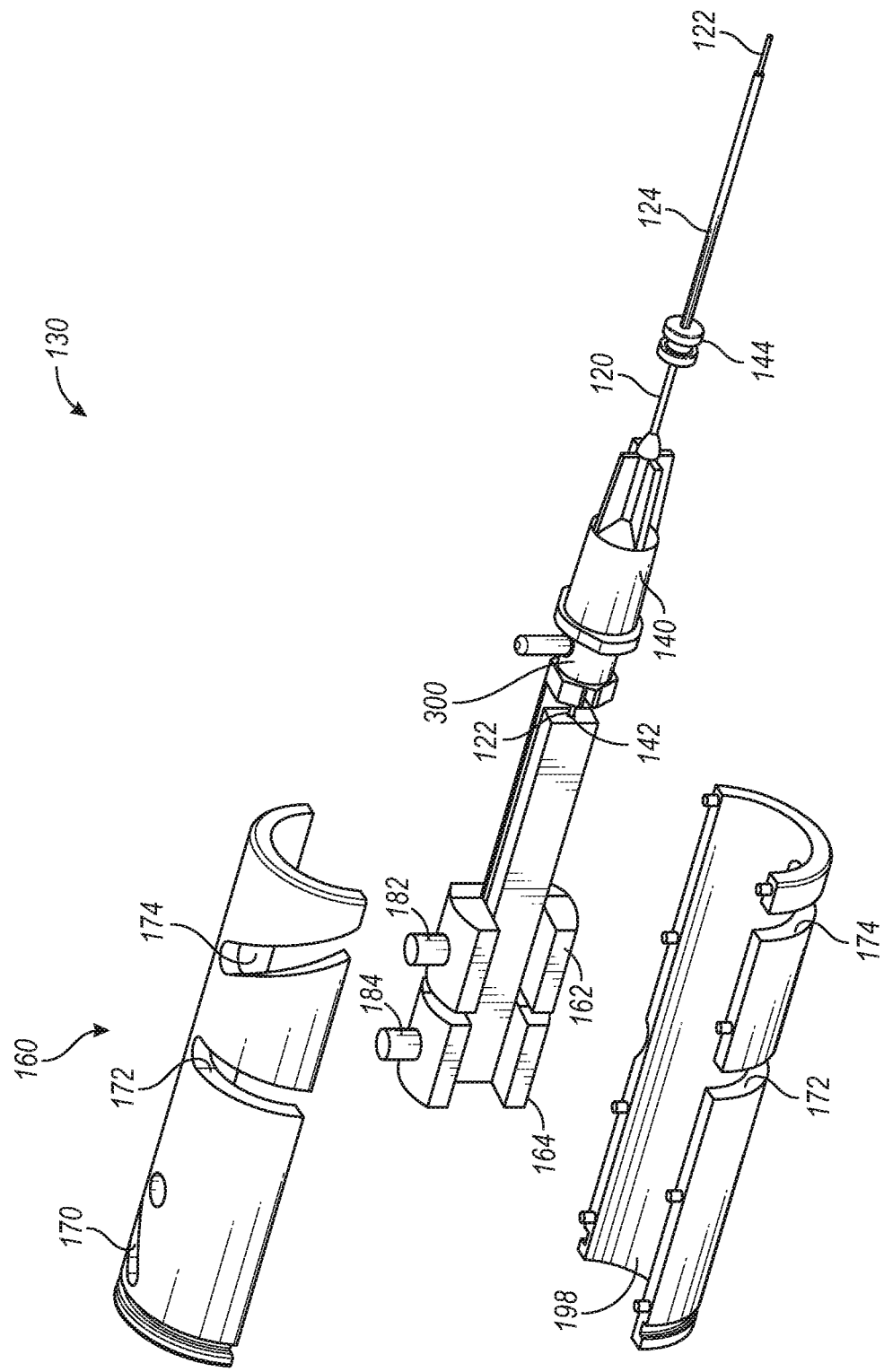
FIG. 3 is a perspective, exploded view of a drive assembly of the inserter shown in FIG. 1B, according to some embodiments.

Referring to FIGS. 2 and 3, the needle component 120, the plunger 122, and the sleeve component 124 can be operably coupled to the drive assembly 130 and/or the housing 102. For example, the needle component 120 can be coupled to a needle mount 140. The needle mount 140 can be fixedly coupled to a proximal end portion of the needle component 120 such that rotational and longitudinal movement between the needle component 120 and the needle mount 140 is restricted or prevented. The needle mount 140 can be enclosed within a distal end portion of the housing 102 when the inserter 100 is assembled. Further, as illustrated in FIG. 3 and discussed further below, the needle mount 140 can be coupled to a needle driver 164 (and in the illustrated embodiment, via a rotational adjustment component 300) of the drive assembly 130.

Further, as shown in FIG. 3, the plunger 122 can be coupled to a plunger mount 142. The plunger mount 142, can be fixedly coupled to a proximal end portion or midsection of the plunger 122 to restrict or prevent rotational and longitudinal movement of the plunger 122 relative to the plunger mount 142. Further, as illustrated in FIG. 3 and discussed further below, the plunger mount 142 can be coupled to a plunger driver 162 of the drive assembly 130.

Furthermore, the sleeve component 124 can be coupled to a sleeve mount 144. The sleeve mount 144 can be coupled to a proximal end portion of the sleeve component 124 so as to prevent rotational and longitudinal movement between the sleeve component 124 and the sleeve mount 144. The sleeve mount 144 can be coupled to a portion 148 of the housing 102, as discussed below.

As noted above, the needle component 120, the plunger 122, and the sleeve component 124 can be operably coupled to the drive assembly 130 and/or the housing 102. Such coupling can occur via the needle mount 140, the plunger mount 142, and the sleeve mount 144. In turn, the needle mount 140, the plunger mount 142, and the sleeve mount 144 can be coupled to one or more drive components that engage with the drive assembly 134 to the housing 102.

In accordance with some embodiments, the drive assembly 130 can be coupled to the needle component 120 and the plunger 122 to actuate movement along the longitudinal axis 178 of the needle component 120 and the plunger 122 relative to the housing 102. For example, the drive assembly 130 can be configured to rotate or slide within the housing 102. The drive assembly 130 can transfer a longitudinal or axial force along the longitudinal axis 178 to the needle component 120 and/or the plunger 122, independently or at the same time, to result in movement of the needle component 120 and the plunger 122 relative to the housing 102 along the longitudinal axis 178.

As discussed herein, motion of the slider component 106 can result in motion of the drive assembly 130 and thereby result in motion of components of the drive assembly 130 relative to the housing 102. Some embodiments can be configured such that the slider component 106 can be longitudinally movable or slidable along the longitudinal axis 178 relative to the housing 102 in order to drive or result in linear motion of the needle component 120 and the plunger 122 and consequently a shunt.

As shown in FIG. 3, the drive assembly 130 can comprise a drive component 160, a plunger driver 162, and a needle driver 164. In some embodiments, longitudinal or linear motion of the slider component 106 along the longitudinal axis 178 can be converted to result in rotation of the drive component 160 of the drive assembly 130, which can then be converted to result in longitudinal or linear motion of the needle component 120 and the plunger 122 along the longitudinal axis 178 relative to the housing 102. In accordance with some embodiments, motion of the components along the longitudinal axis 178 can be parallel relative to the longitudinal axis 178.

FIG. 3 also illustrates an embodiment of the drive component 160. The drive component 160 can comprise a groove 170 that can be configured to engage with a corresponding protrusion (not shown) of the slider component 106. Further, the drive component 160 can also comprise first and second driving grooves 172, 174 that can be configured to slidingly engage corresponding protrusions of the plunger driver 162 and the needle driver 164. Thus, the slider component 106 can comprise a protrusion 430 (shown in FIG. 4B), the plunger driver 162 can comprise a protrusion 182, and the needle driver 164 can comprise a protrusion 184. This arrangement of slots and protrusions can facilitate the transfer of motion from the slider component 106 to the respective ones of the needle component 120 and the plunger 122. Further, the plunger driver 162 and the needle driver 164 can comprise rounded bodies that contact and slide against an inner guide surface 198 of the drive component 160 when seated within the drive component 160.

Figure 4A:
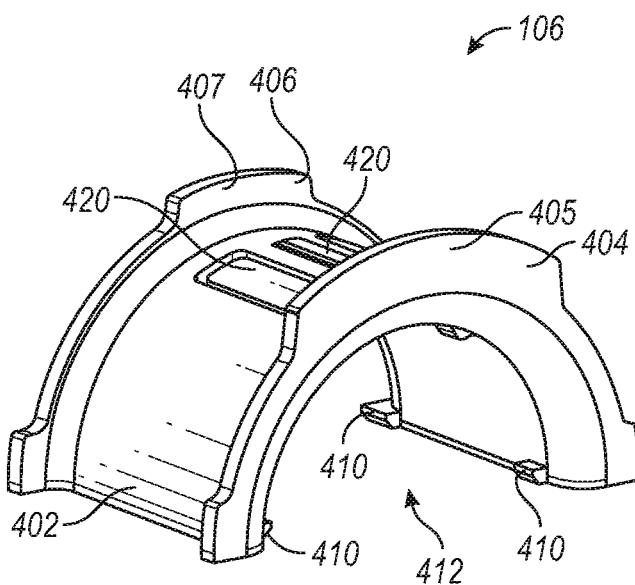
FIGS. 4A-4C illustrate a slider component of the inserter shown in FIG. 1B, according to some embodiments.
Figure 4B:
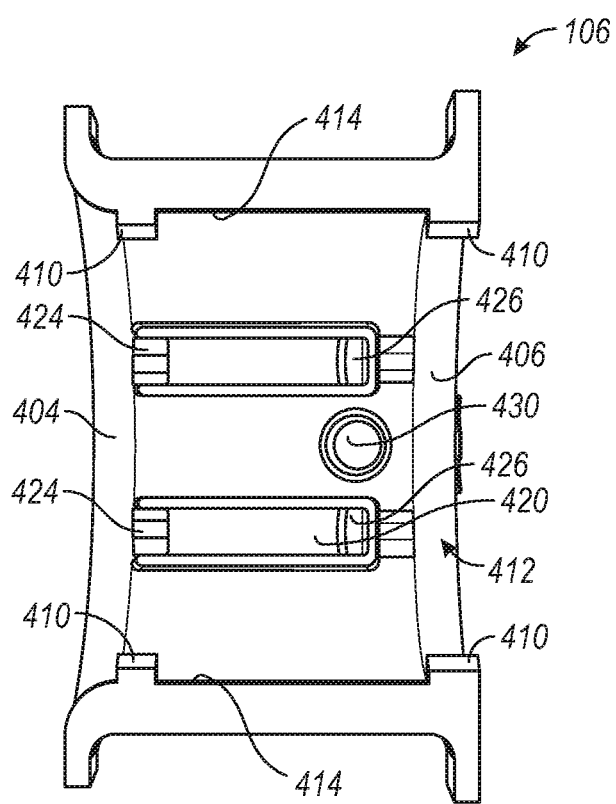
Figure 4C:
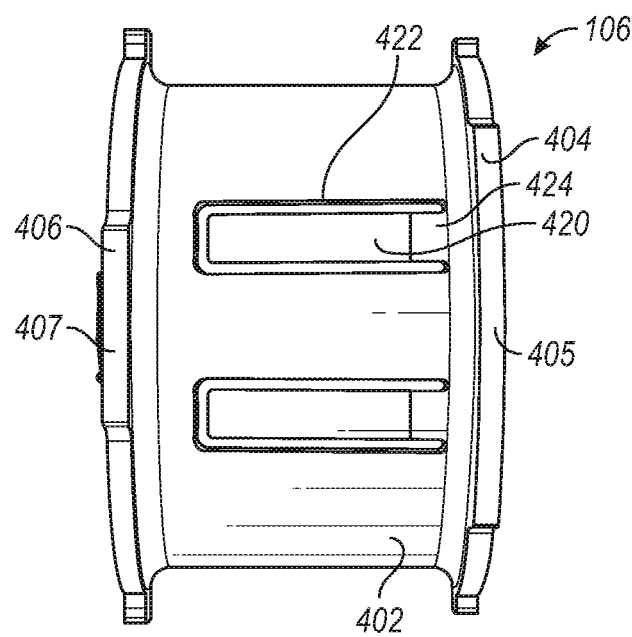

FIGS. 4A-4C illustrate the slider component 106 of the inserter 100 shown in FIG. 1B, according to some embodiments. FIG. 4A illustrates a perspective view of the slider component 106. The slider component 106 can comprise a slider body 402 with a proximal end portion 406 and a distal end portion 404. The slider body 402 can have a generally semi-cylindrical shape. The proximal end portion 406 and the distal end portion 404 can comprise a raised distal boundary or edge 405 and a raised proximal boundary or edge 407 that protrude radially from the slider component 106 in order to provide a secure, ergonomic grip with a thumb or finger of the operator during use.

The slider component 106 can comprise one or more guide tabs 410. The guide tabs 410 can be disposed at the distal end portion 404 and the proximal end portion 406. For example, the guide tabs 410 can extend inwardly toward an interior region 412 of the slider component 106. The interior region 412 of the slider component 106 can comprise a generally semi-cylindrical shape or cavity that can be configured to be coupled to the inserter 100, such as by receiving a portion of the inserter 100 therein. When coupled to the inserter 100, the guide tabs 410 can be disposed within the guide channel 111 of the housing 102 to couple the slider component 106 to the housing 102. Thus, the guide tabs 410 of the slider component 106 can be retained within the guide channel 111, thereby restraining radial movement of the slider component 106 relative to the housing 102 while allowing for axial or longitudinal movement of the slider component 106 along the housing 102, as described herein.

Optionally, the slider component 106 can be configured to include a plurality of guide tabs 410 extending radially inwardly into the interior region 412 from opposing faces or edges of the slider component 106. For example, as illustrated in FIG. 4B, the slider component 106 can comprise a pair of guide tabs 410 extending radially inwardly from interior side edges 414 of the slider component 106. The guide tabs 410 can be spaced between about 90 degrees to about 180 degrees apart from each other along the interior side edges 414 or an inner surface of the interior region 412.

Further, in some embodiments, the guide tabs 410 can be beveled to allow the slider component 106 to be pressed or snapped onto the housing 102 and into the guide channel 111. For example, one or more of the guide tabs 410 can comprise a beveled portion facing away from the interior region 412. Thus, when the slider component 106 is pressed onto the housing 102, the slider component 106 can deflect slightly to open the interior region 412 until the guide tabs 410 snap into place in the guide channels 111.

FIG. 4B illustrates a bottom view of the slider component 106. Referring to FIG. 4B, the protrusion 430 can be formed integrally with the body 402 of the slider component 106. However, in accordance with some embodiments, the protrusion 430 can also be formed as a separate component that is later attached to the body 402 of the slider component 106. As described herein, the motion of the slider component 106 can be transmitted to the drive assembly 130 via the protrusion 430 and thereby result in motion of the components of the drive assembly 130 relative to the housing 102. In some embodiments, the protrusion 430 can be disposed at the proximal end portion 406 of the slider component 106. In some embodiments, the protrusion 430 can be disposed at the distal end portion 404 of the slider component. In some embodiments, the protrusion 430 can be disposed in between the proximal end portion 406 and the distal end portion 404.

FIG. 4C illustrates a top view of the slider component 106. With reference to FIGS. 4B and 4C, friction tabs 420 can be integrally formed with the body 402 of the slider component 106. As used herein, "integrally formed" can be defined as being formed as a single, continuous component or piece. Such components can be injection molded as a single, continuous component or begin as a single part that is later machined or otherwise processed to create various features that are coupled together from a single, continuous material. For example, through a process such as injection molding or laser beam machining, the friction tabs 420 can be formed by creating slots 422 that thereby define shape of the friction tab 420 and allow the friction tab 420 to move relative to the body 402. The friction tab 420 can be attached to the body 402, such as by a cantilevered connection or via pivots or attachment points 424. The attachment points 424 can be reinforced or include additional body material to improve cycle fatigue strength. In some embodiments, the friction tabs 420 can be formed as a separate component that are later attached to the body 402 of the slider component 106.

As shown in FIG. 4B, the friction tab 420 can include a biasing member or friction protrusion 426 which extends radially beyond adjacent portions of the body 402. The protrusion 426 can extend radially inwardly toward or into the interior region 412. The protrusion 426 can be tapered or beveled in shape to allow the slider component 106 to travel over one or more engagement structures, such as the notches, serrations, slots, protrusions, or bumps, of the housing 102 in one direction and resist direction in an opposite direction.

For example, the protrusion 426 can comprise a deflection-facilitating distal surface that extends at an obtuse angle with respect to an inner surface of the slider component 106 and faces the distal boundary or edge 405. As such, in some embodiments, the friction tab 420 can be moveable or deflectable relative to the body of the slider component 106, and the distal surface of the protrusion 426 can permit the protrusion 426 to begin radial deflection as it slides axially over an engagement structure formed on the housing 102. Such a configuration is illustrated in the side view of FIG. 6A. The distal surface of the protrusion 426 can therefore be configured to permit or facilitate distal motion of the slider component 106 along the housing 102.

Further, the protrusion 426 can comprise an anti-reversing proximal surface that extends perpendicularly from or at an angle (e.g., if a protrusion, at an acute angle, or if a notch, at an obtuse angle) with respect to the inner surface of the slider component 106 and faces the proximal boundary or edge 407. The proximal surface of the protrusion 426 can therefore be configured to catch or restrict proximal motion of the slider component 106 along the housing 102.

In some embodiments, the engagement structure of the housing 102 can comprise a deflection-facilitating cross-sectional profile, such as a rounded shape or angled shape (e.g., extending an obtuse angle from an outer surface 440 of the housing 102) along a proximal-facing portion of the engagement structure that initially contacts the protrusion 426 as the slider component 106 is advanced distally along the housing 102. Further, in some embodiments, both the proximal-facing portion and a distal-facing portion of the engagement structure can comprise a deflection-facilitating cross-sectional profile.

Optionally, the engagement structure of the housing can comprise an anti-reversing cross-sectional profile. For example, the engagement structure can comprise an edge that extends perpendicularly or at an angle (e.g., if a protrusion, at an obtuse angle, or if a notch, at an acute angle) from the outer surface 440 of the housing 102. In some embodiments, the distal-facing portion of the engagement structure can comprise the anti-reversing cross-sectional profile. Thus, the distal-facing portion of the engagement structure can catch with or engage the proximal surface of the protrusion 426 to restrict proximal motion of the slider component 106 along the housing 102. Additionally, in some embodiments, the proximal-facing portion of the engagement structure can comprise a deflection-facilitating cross-sectional profile and the distal-facing portion of the engagement structure can comprise an anti-reversing cross-sectional profile.

Optionally, as described further herein, the protrusion 426 and/or the engagement structure can be shaped to provide audible and/or tactile feedback to the operator. As will be appreciated by personal skill in the art, a snap or click can be created by deflecting the friction tab 420 and quickly permitting release of the friction tab 420 into contact with the outer surface 440 of the housing 102. This can be accomplished in a variety of ways, including when the engagement structure includes a perpendicular portion that would permit the protrusion 426 of the friction tab 420 to rapidly move radially into contact with the outer surface 440 of the housing 102. For example, the distal-facing portion of the engagement structure can extend perpendicularly relative to the outer surface 440 of the housing 102 such that distal advancement of the slider component 106 over the engagement structure permits the protrusion 426 to snap radially inwardly against the outer surface 440 of the housing 102, thereby providing audible and/or tactile feedback to the operator.

Figure 5:
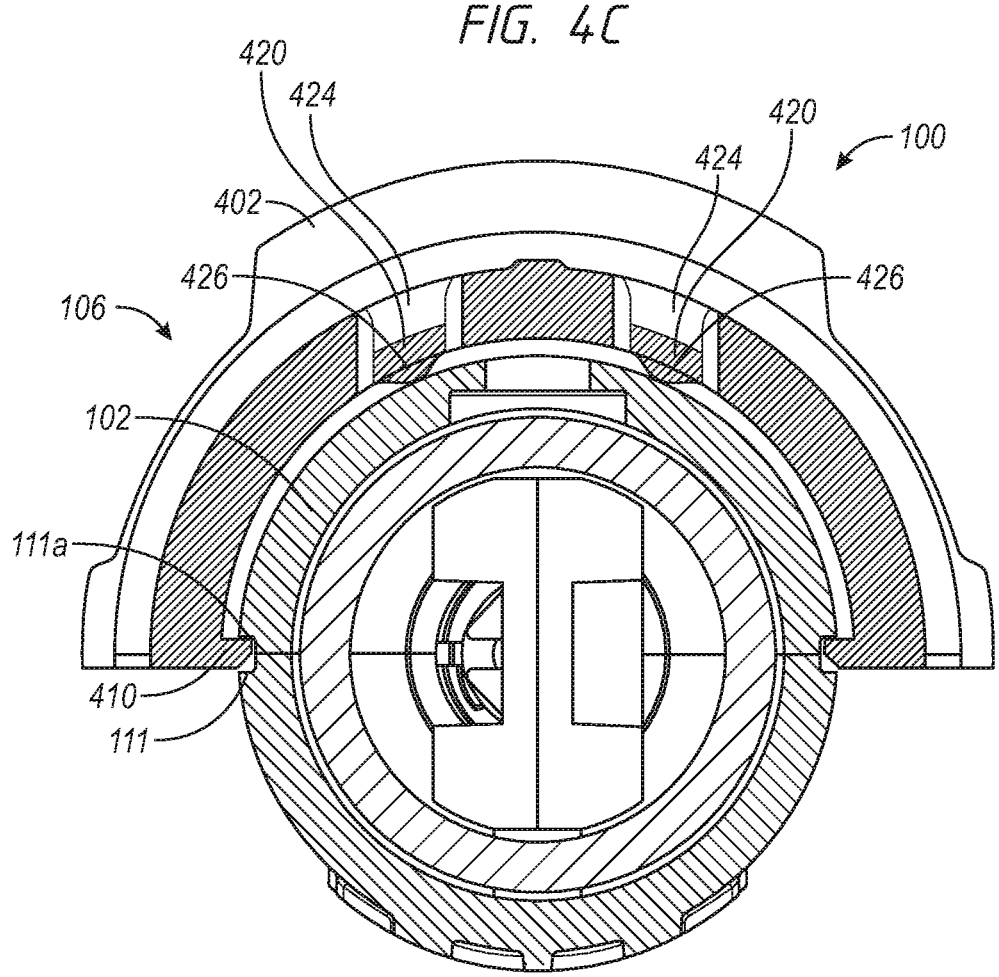
FIG. 5 is a cross-sectional view of an inserter for implanting an intraocular shunt into an eye, according to some embodiments.

Referring to FIG. 5, an embodiment of an inserter 100 is shown with the slider component 106 attached to the housing 102 by engaging the guide tabs 410 within the guide channels 111. In some embodiments, the guide channels 111 are disposed on opposite sides of the housing 102. For example, the guide tabs 410 and/or the guide channels 111 can be oriented at different angular locations along the slider component 106 and/or the housing 102, such at about 180 degrees away from each other, less than 180 degrees away from each other, less than 170 degrees away from each other, less than 160 degrees away from each other, or less than 150 degrees away from each other.

When the slider component 106 is engaged in the guide channels 111, the protrusions 426 can contact portions of the housing 102. For example, the protrusions 426 can contact the housing 102 adjacent to the slot 110. In some embodiments, the protrusions 426 can be positioned to contact the housing 102 on opposing sides of the slot 110.

The protrusions 426 may be biased into contact with the housing 102. In some embodiments, the protrusions 426 can contact the housing 102 and cause the friction tabs 420 to be urged or deflected radially away from the housing 102, e.g., by deforming along the length of the friction tabs 420 or at the attachment points 424. In some embodiments, body of the friction tabs 420 and/or the attachment points 424 can resist this deflection or deformation, providing a reaction force via the friction tabs 420 and the protrusions 426 against the housing 102. In some embodiments, the attachment points 424 and the friction tabs 420 can be biased to provide a biasing force. This biasing force can urge the slider component 106 radially away from the housing 102, thereby causing the guide tabs 410 of the slider component 106 to be pressed against the inside of the guide channel 111. Thus, although the guide tabs 410 limit the radial outward motion of the slider component 106 relative to the housing 102, the biasing force exerted via the friction tabs 420 can increase the friction between the slider component 106 and the housing 102. Therefore, in some embodiments, the slider component 106 can tend to remain stationary along the housing 102 unless a sufficient axial force is exerted against the slider component 106 to overcome the friction between the slider component 106 on the housing 102.

For example, as shown in FIG. 5, as the slider component 106 is forced radially away from the housing 102, the guide tabs 410 move toward a channel wall 111a of the guide channel 111. Therefore, in a resting state the slider component 106 is frictionally retained between the guide tabs 410 and the channel wall 111a and the protrusions 426 of the friction tabs 420 against the outer surface of the housing 102. Advantageously, this arrangement also minimizes radial play within the slider component 106 relative to the housing 102.

Additionally, by engaging the friction tabs 420 and the guide tabs 410 against the housing 102, the friction force between the slider component 106 and the housing 102 is enhanced. This can allow for the slider component 106 to be retained in a desired or initial position, and can prevent inadvertent movement of the slider component 106 during shipping and handling of the inserter 100. Therefore, to move the slider component 106 and thereby operate the inserter, the frictional force of the slider component 106 relative to the housing 102 must be overcome by a deliberate, intentional axial force exerted by the operator.

Figure 6A:
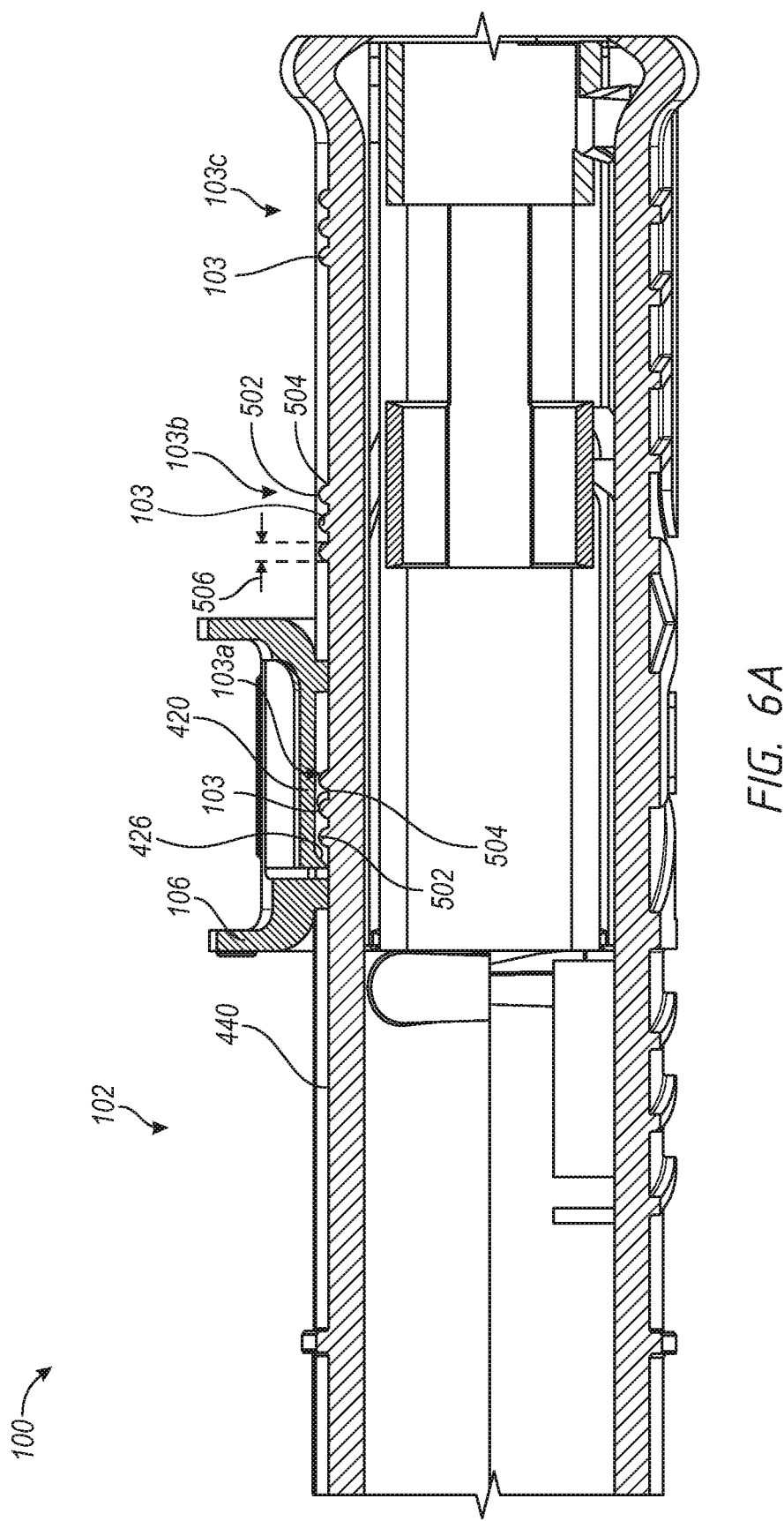

Referring to FIG. 6A, the friction tabs 420 can further provide tactile and audible feedback to the operator during operation of the inserter 100. During operation, as the slider component 106 is advanced relative to the housing 102, the friction tabs 420, and more particularly, the friction protrusions 426 can pass over engagement structures 103 formed on the housing 102. Each engagement structure 103 can comprise a discontinuity in an outer surface 440 of the housing 102, such as such as a notch, serration, slot, protrusion, or bump. The engagement structures 103 can be indexed to reflect different stages of operation of the inserter 100 or positions of the slider component 106 along the housing 102 or slot 110. The housing 102 can be configured to include one or many engagement structures 103. Further, the engagement structures can be grouped together (as a single group or multiple groups) or spaced apart along the housing 102.

Figure 6B:
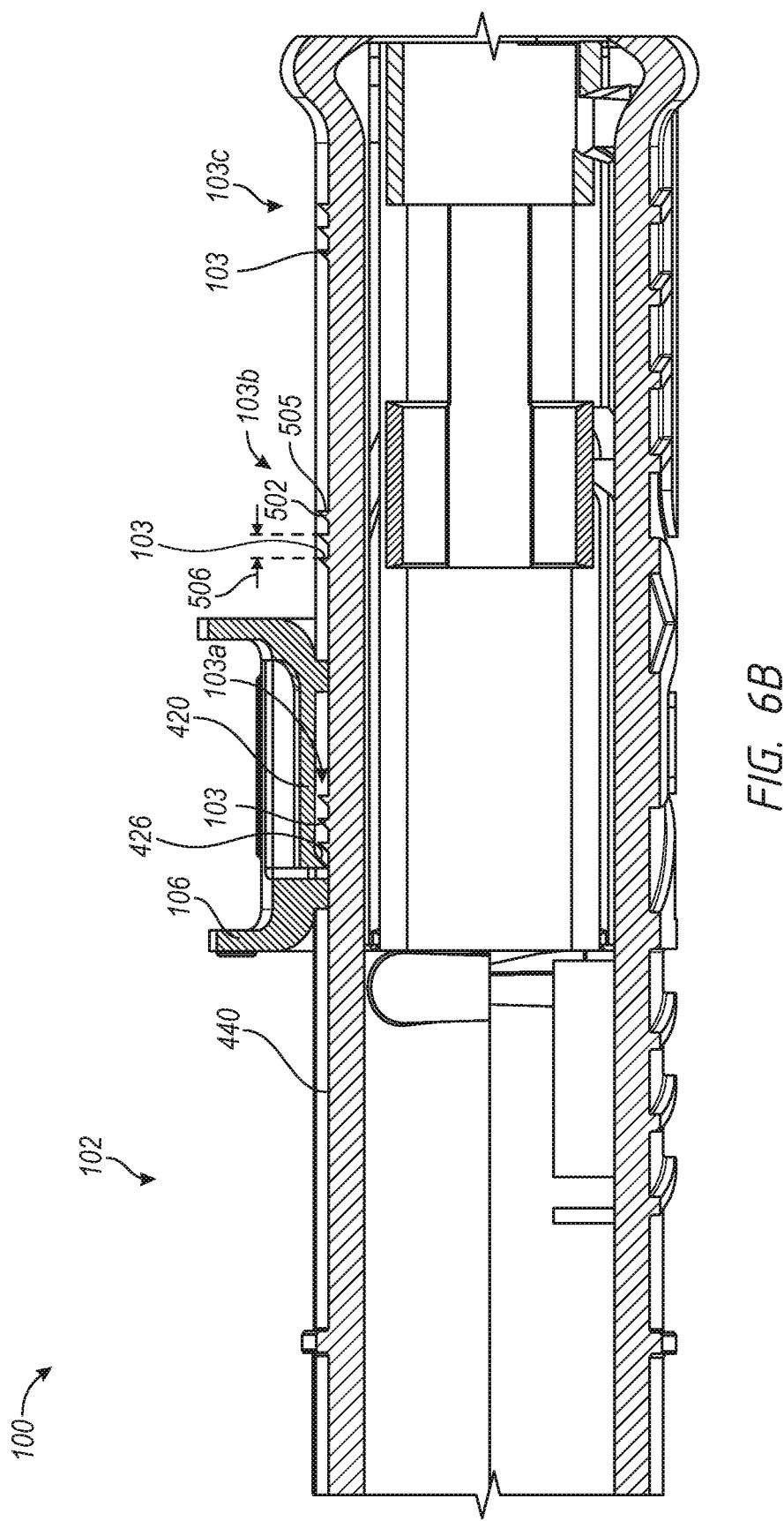

For example, as shown in FIGS. 6A-6C, the engagement structures 103 can be configured such that in order for the slider component 106 to move away from its initial position, the friction tabs 420 contact against a first engagement structure 103a (shown as a group of three engagement structures 103, although the first engagement structure 103a can also comprise just a single engagement structure 103 or two engagement structures 103) in the housing 102. Similarly, just before the slider component 106 reaches a certain location long its full travel path (e.g., halfway along the travel path or after the shunt inserter has exposed the shunt within the eye and just before continued advancement of the slider begins to retract the needle of the inserter back into the housing), the friction tabs 420 can contact against a second engagement structure 103b (shown as a group of three engagement structures 103, although the second engagement structure 103b can also comprise just a single engagement structure 103 or two engagement structures 103). Finally, the friction tabs 420 can click against a third engagement structure 103c (shown as a group of three engagement structures 103, although the third engagement structure 103c can also comprise just a single engagement structure 103 or two engagement structures 103) when the slider component 106 has advanced sufficiently to release the shunt. The feedback can be used to signal that the inserter 100 is performing a different operation, that the shunt or a portion of the inserter 100 has reached a certain position, and/or that the different operation can require a different actuation force.

Thus, the slider component 106 can move along the housing 102 and provide tactile and/or audible feedback to the operator regarding a position of the slider component 106 relative to the housing 102 and/or a position of the shunt or a stage of shunt delivery. In some embodiments, it may be advantageous to provide feedback to the operator when the shunt is initially exposed from the needle of the inserter. Further, it may also be advantageous to provide feedback to the operator when the inserter has released the shunt (which may not yet be fully exposed outside of the needle).

The type, frequency, and/or strength of tactile and/or audible signals can vary depending on the position of the slider component 106, the shunt, and/or the state of shunt delivery.

A tactile or audible signal may be provided only when certain milestones were achieved, such as initial movement of the slider component, initial shunt exposure of the shunt, a position prior to full release of the shunt (such as when the sleeve has been retracted halfway from its fully extended position), and/or reaching a final position of the slider component when the shunt is fully released and the needle is fully retracted (or other such positions, as discussed in U.S. Pat. No. 9,585,790, the entirety of which is incorporated herein by reference). Further, some embodiments can be provided in which tactile feedback is provided only at certain milestones while audible feedback is provided at other milestones. For example, either one of tactile or audible feedback can be provided at the beginning stages while the other one of tactile or audible feedback is provided at the latter stages of the procedure. Further, either one of tactile or audible feedback can be provided at the beginning and at the end to mark initial and final slider component movement, while the other one of tactile or audible feedback is provided when the shunt is initially exposed and just prior to full release of the shunt. Various options and permutations of the above can be provided.

Optionally, the housing 102 can comprise a plurality of engagement structures 103 that provide a continuous, modest tactile or audible feedback to the operator to indicate that the slider component 106 is being advanced.

Therefore, in accordance with some embodiments, the shape of the engagement structures 103 can be varied along the length of the housing 102 to provide varying types, frequencies, and/or strengths of tactile or audible feedback and/or to increase the degree of resistance to the operator's force required to be exerted to move the slider component.

For example, with regard to the degree of resistance provided by the engagement structures 103, in some embodiments, the engagement structures 103 can be configured to require the operator to overcome a successively higher degree of resistance as the shunt is being exposed and eventually released from the inserter. Thus, the size (e.g., height or axial length) of the engagement structures 103 can increase in a distal direction to thereby create an increasing degree of resistance against the distal advancement of the slider component.

The engagement structures 103 can define at least one notch, serration, slot, protrusion, bump, or other modified surface to provide tactile and/or audible signals or feedback to the operator. Referring to FIGS. 6A-6C, various features of the engagement structures 103 are shown. As shown in FIG. 6A, the engagement structure 103 can include one or more notches, serrations, slots, protrusions, or bumps having an outer or cross-sectional profile 502 that can comprise deflection-facilitating surfaces and/or anti-reversing surfaces. The radius 504 and the spacing 506 of the engagement structures 103 can be altered. In particular, the radius 504 of the engagement structures 103 can be altered to provide stronger feedback or to resist motion of the slider component 106.

As shown in FIG. 6B, the engagement structure 103 can include a perpendicular distal-facing surface 505 that provides a substantial drop from the tip or height of the engagement structure 103. In some embodiments, the surface 505 can provide an auditory function as the friction tab 420 is permitted to ride up the profile 502 on a leading or proximal side and then, the friction tab 420 springs, snaps, or clicks downwardly or radially inwardly against the housing 102 to provide an audible and/or tactile signal.

In accordance with some embodiments, the radius or angle of the profile 502 or the height of the engagement structure 103 can be modified to provide a different sound, tactile signal, or to increase sliding resistance against the slider component 106 as the slider component 106 is across the engagement structure 103.

Optionally, when the engagement structures 103 are grouped together, the spacing between the engagement structures 103 can be altered to change the frequency of occurrence of the audible signals from the auditory mechanism of the friction tab 420.

As shown in FIG. 6C, the engagement structures 103 can comprise a cross-sectional profile 502 having tapered peaks. The tapered peaks may provide a different audible and/or tactile feedback compared to the features of the bumps or serrated structures shown in FIGS. 6A and 6B. Similar to the structures illustrated in FIGS. 6A and 6B, the height and the spacing of the tapered peaks can be altered to provide a desired audible or tactile signal.

In some embodiments, different engagement structures 103 can utilize different features to provide different signals to an operator. In some embodiments, a single engagement structure 103 can utilize a combination of the features described in FIGS. 6A-6C.

Figure 7A:
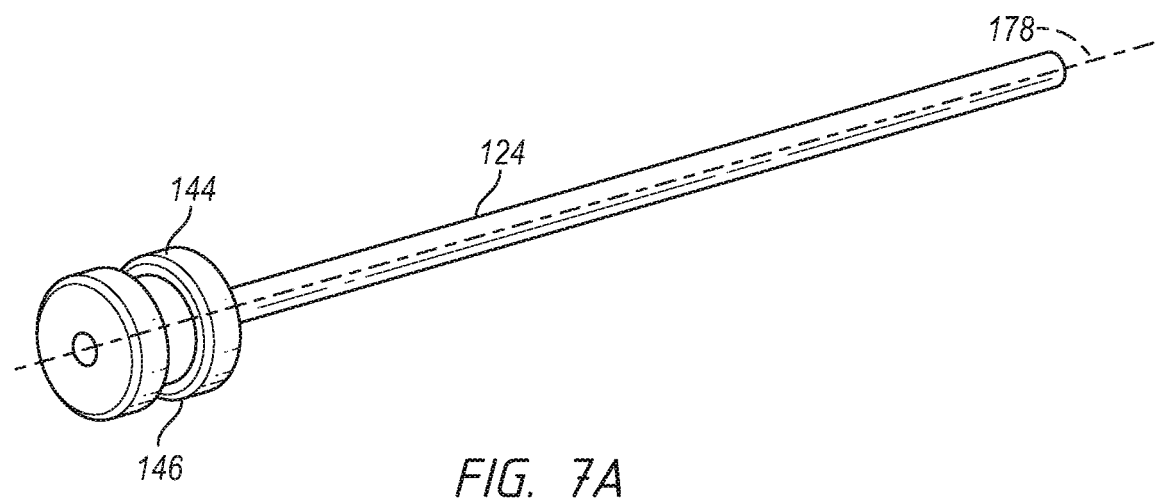
FIG. 7A is a perspective view of a sleeve mount of the drive assembly shown in FIG. 3, having a straight shaft, according to some embodiments.
Figure 7B:
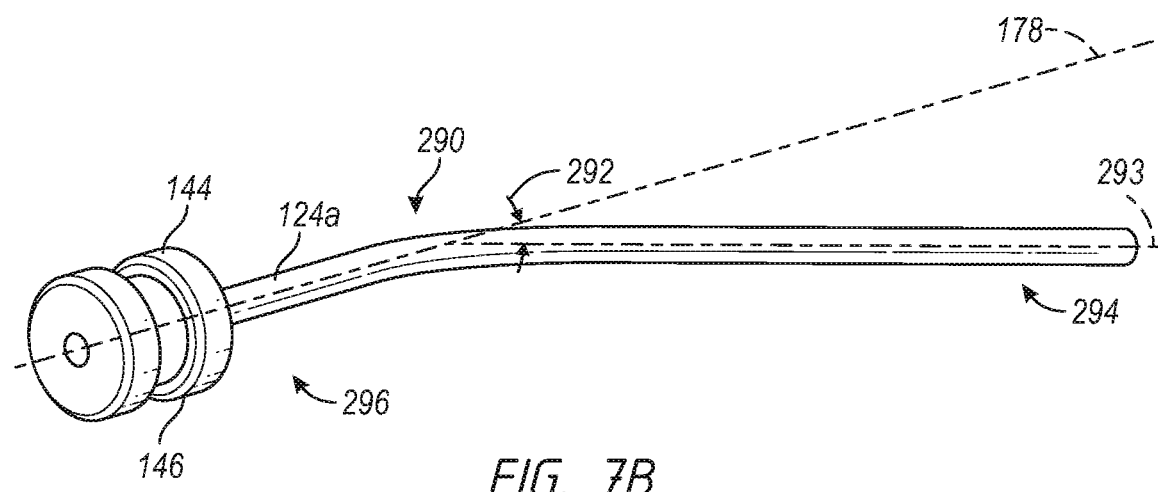
FIG. 7B is a perspective view of a sleeve mount of the drive assembly shown in FIG. 3, having a bended shaft, according to some embodiments.

As illustrated, FIG. 7A is a perspective view of a sleeve mount 144 coupled to a straight sleeve component 124, as also shown and discussed above in the embodiment of FIG. 2. However, the sleeve component can also be configured to comprise a bend, as illustrated in FIG. 7B. FIG. 7B illustrates a sleeve component 124a that has a slight curve or bend 290. The bend 290 can be adjacent to the sleeve mount 144 and provide an angular deviation 292 of an axis 293 of the sleeve component 124a from the longitudinal axis 178 within a range of between about 3 degrees to about 30 degrees, between about 4 degrees to about 15 degrees, between about 5 degrees to about 13 degrees, or of about 8 degrees relative to the longitudinal axis of the inserter 100.

The bend in the sleeve component 124a can improve the accessibility to areas of the eye, such as when the inserter approaches the eye from a position in which the inserter is positioned above the cheekbone.

Additionally, as illustrated, an insertion or distal end portion 294 of the sleeve component 124a can be substantially straight while a deployment or proximal end portion 296 of the sleeve component 124a can comprise a curve or bend. Further, in some embodiments, the distal end portion 294 and the proximal end portion 296 can both comprise a bend or be straight with a bend section disposed therebetween. The proximal end portion 296 can be about a quarter to about a half of the overall length of the sleeve component 124a. In some embodiments, the length of the proximal end portion 296 can be about one third of the length of the sleeve component 124a. Accordingly, in some embodiments, the distal end portion 294 can be about a half to about three quarters of the length of the sleeve component 124a, and in some embodiments, about two thirds of the length of the sleeve component 124a. Advantageously then, the distal end portion 294 of the sleeve component 124a can be of a sufficient length such that the entirety of the sleeve component 124a that enters the eye is substantially straight.

While the sleeve component 124a can comprise a rigid structure that can withstand typical bending stresses in performing embodiments of the procedures disclosed herein, the needle component 120 can be made from a flexible shaft that can deflect during proximal withdrawal of the needle component 120 into the sleeve component 124a.

Thus, a proximal portion of the needle component 120 that extends along the bend 290 of the sleeve component 124a can be proximally withdrawn into the sleeve component 124a proximal or adjacent to the sleeve mount 144. After such motion, although the proximal portion of the needle component 120 was bended, that same portion of the needle component 120 can flex and straighten out as the needle component 120 is pulled proximally into a straight portion of the needle component 120 or other components within the inserter. Additionally, portions of the needle component 120 that reside in the distal end portion of the sleeve component 124*a* (and are therefore in a straight configuration) can be flexed or deflected into a curved or bended configuration when the needle component 120 is proximally retracted through the bend 290 of the sleeve component 124*a*.

Accordingly, the use of an arcuate or bent sleeve component 124*a* in combination with a flexible or conforming needle component 120 can allow some embodiments of the inserter to provide improved accessibility to areas of the eye.

Some embodiments can implement aspects of the sleeve structures and methods of use disclosed in applicant's U.S. Patent Application Publ. No. 2012/0123434, the entirety of which is incorporated herein by reference.

Referring to FIG. 8A-10A, in some embodiments, it may be desirable that the shaft or needle component 120 comprise a bend for some of the reasons discussed herein. In some embodiments, the bend can be between about 1 degree and about 20 degrees, about 2 degrees and about 18 degrees, about 3 degrees and about 16 degrees, about 4 degrees and about 14 degrees, about 3 degrees and about 16 degrees, about 5 degrees and about 12 degrees, about 6 degrees and about 10 degrees, or about 1 degrees, about 2 degrees, about 3 degrees, about 4 degrees, about 5 degrees, about 6 degrees, about 7 degrees, about 8 degrees, about 9 degrees, about 10 degrees, about 11 degrees, about 12 degrees, about 13 degrees, about 14 degrees, about 15 degrees, about 16 degrees, about 17 degrees, about 18 degrees, about 19 degrees, or about 20 degrees.

Optionally, in some embodiments, the needle component 120 can be held in a bended configuration. In accordance with some embodiments, the sleeve component 124 can be straight and/or selectively angled or bent with the use of a removable or retrofittable end component, deflector component, or alignment guide 602. In some embodiments, an inserter 100 can be delivered with an alignment guide 602 coupled to the inserter 100 or disposed over the sleeve component 124.

Figure 8A:
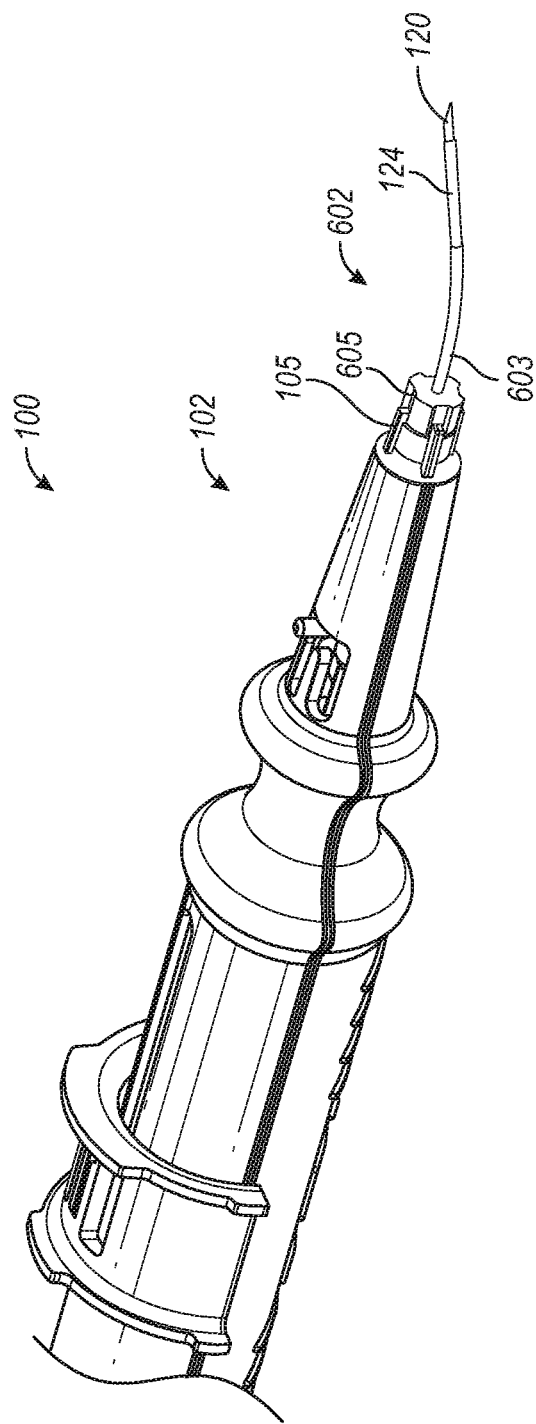
FIG. 8A is a perspective view of an inserter having an alignment guide for providing a bend in the shaft of the inserter, according to some embodiments.

Referring to FIG. 8A, the alignment guide 602 can comprise a hollow guide shaft 603 that is coupled to an attachment portion 604. The attachment portion 604 can be keyed or indexed in order to rotationally orient the alignment guide 602 relative to the housing 102 of the inserter 100. For example, the attachment portion 604 can serve to couple the alignment guide 602 to the housing 102 in a desired angular or rotational orientation in order to set a bend direction and/or of the needle relative to the longitudinal axis of the housing 102 of the inserter 100.

In some embodiments, the hollow guide shaft 603 can be disposed over portions of the sleeve component 124 and the needle component 120. The guide shaft 603 can have an angle similar to or determine the angle of the angled sleeve component described herein. For example, the alignment guide 602 can bend the sleeve component 124 and the needle component 120 at a bend 690 and provide an angular deviation 692 of an axis 693 of the guide shaft 603 from a longitudinal axis 178 of the inserter 100 within a range of between about 0 degrees and about 30 degrees, between about 0 degrees and about 20 degrees, between about 0 degrees and about 15 degrees, or at about 8 degrees relative to the longitudinal axis of the inserter.

Thus, in some embodiments, an operator can modify a needle of an inserter by applying the alignment guide to the inserter, thereby bending the needle to a desired angular orientation. The alignment guide can be provided as part of a set of alignment guides that have different angular orientations. The alignment guide can be retrofittable to any existing inserter. Further, the alignment guide can be configured to mate with distal end portion of inserter in order to securely engage the alignment guide rotationally and longitudinally relative to the inserter.

For example, in some embodiments, the operator can rotate the needle until the bevel begins to push the conjunctiva away from the sclera, as discussed and shown in U.S. Pat. No. 9,585,790, the entirety of which is incorporated herein by reference. This procedure, which can be referred to as "tenting" the conjunctiva, can create a small space or gap between the conjunctiva and the sclera adjacent to the bevel of the needle. Once a space has been created by tenting the conjunctive, a shunt can be advanced into the space from the needle. As a result, the shunt can be substantially easier to push into the space because the conjunctiva has been pushed away and is not immediately obstructing the advancement of the shunt into the subconjunctival space.

Additionally, in some embodiments, an insertion or distal end portion 694 of the guide shaft 603 can be substantially straight while a deployment or proximal end portion 696 of the guide shaft 603 can comprise a curve or bend. Further, in some embodiments, the distal end portion 694 and the proximal end portion 696 can both comprise a bend or be straight with a bend section disposed therebetween. The proximal end portion 696 can be about one quarter to about one half of the overall length of the guide shaft 603. In some embodiments, the length of the proximal end portion 696 can be about one third of the length of the guide shaft 603. Accordingly, in some embodiments, the distal end portion 694 can be about one half to about three quarters of the length of the guide shaft 603, and in some embodiments, about two thirds of the length of the guide shaft 603.

The alignment guide 602 can allow an operator to modify the angle of the sleeve component 124 and the needle component 120 prior to a procedure (e.g., by permitting the operator to select from a variety of different alignment guides having different angular orientations and configurations of relative lengths of the proximal and distal end portions) without having to replace the needle component 120 of the inserter 100. Further, the guide shaft 603 can provide enhanced stiffness to the sleeve component 124 and the needle component 120. In some embodiments, the alignment guide 602 can facilitate the use of thinner gauge needles for the needle component 120, including, but not limited to needles of 28 Gauge or thinner in size. Thus, implementations of the present disclosure can advantageously allow very small, delicate needles to be used in the delivery of an intraocular shunt while ensuring that the needle exhibits sufficient strength and stiffness during the delivery process.

The sleeve component 124 and the needle component 120 can be flexible or elastic to allow deflection when the alignment guide 602 is installed. The alignment guide 602 can be removed to allow the sleeve component 124 and the underlying needle component 120 to move to a default straight configuration. For example, the alignment guide 602 can be configured to elastically deform the sleeve component 124. Thus, upon removal of the alignment guide 602, the sleeve component 124 and the needle component 120 will return to a straight configuration. Further, the alignment guide 602 can be reinstalled on the housing 102, if needed.

Figure 8B:
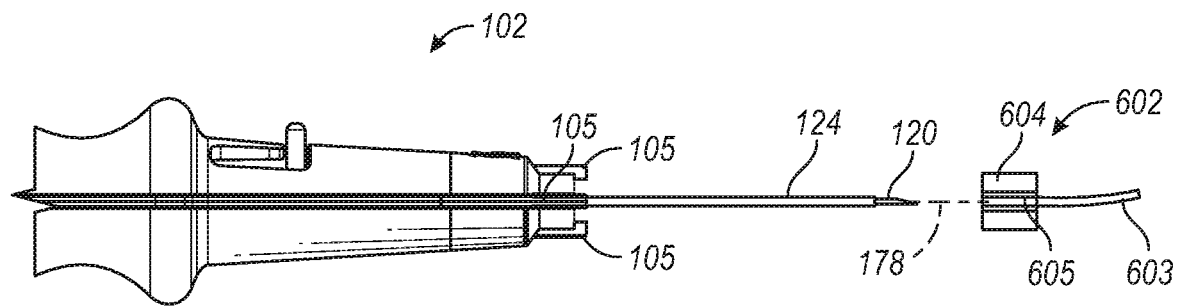
FIG. 8B is a perspective view of an alignment guide coupled to a sleeve, according to some embodiments.
Figure 8C:
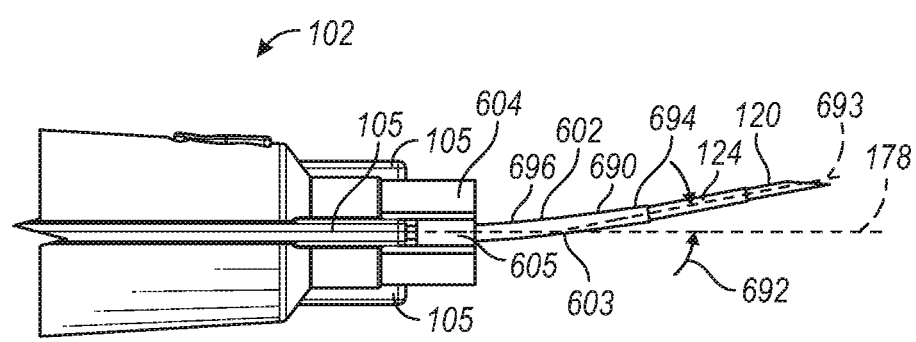
FIG. 8C is a side view of an alignment guide coupled to a sleeve, according to some embodiments.

As shown in FIGS. 8A-8C, in some embodiments, proper rotational alignment of the alignment guide 602 can be facilitated by the attachment portion 604, which can be keyed or indexed, that orients the alignment guide 602 relative to the housing 102. The index grooves 605 of the attachment portion 604 can align with the index protrusions 105 of the housing 102. In some embodiments, the index grooves 605 can be keyed to the index protrusions 105 to allow the alignment guide 602 to attach to the housing 102 in a desired orientation. Thus, the alignment guide 602 and the inserter 100 can be configured to have one or more preset relative orientations. The index grooves 605 can be in the shape of longitudinally extending indentations or slots formed in the attachment portion 604.

Further, the index grooves 605 can be spaced apart from each other (e.g., circumferentially) at equal circumferential distances, and the index protrusions 105 can be spaced apart from each other (e.g., circumferentially) at equal circumferential spacings, so that the alignment guide 602 can be rotated to one or more preset rotational orientations. However, the circumferential distances between the index grooves 605 and/or the index protrusions 105 can vary. In the embodiment illustrated in FIGS. 8A-8C, there are four preset rotational orientations. In some embodiments, the alignment guide 602 can comprise a single index groove 605 that can be mated with a single index protrusion 105 of the housing 102 so that the alignment guide 602 has a single rotational orientation relative to the inserter 100.

The attachment portion 604 can have a number of index grooves 605 that is the same in number as the index protrusions 105. However, in some embodiments, the alignment guide 602 can comprise more index grooves 605 than there are index protrusions 105. For example, although there can be four index protrusions 105 and four index grooves 605, there can be four index protrusions 105 and eight index grooves 605, four index protrusions 105 and twelve index grooves 605, or ratios of index protrusions 105 to index grooves 605 of 1:4, 1:5, 1:6, or more.

Figure 9A:
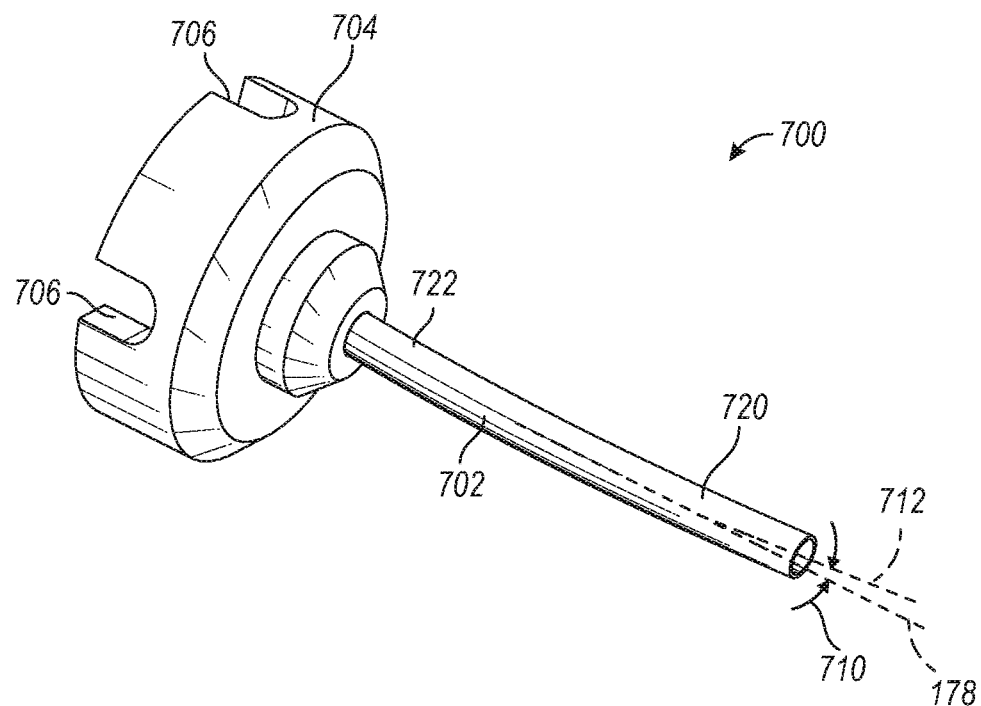
FIG. 9A is a front perspective view of another alignment guide, according to some embodiments.

FIG. 9A is a front perspective view of another retrofittable end component, deflector component, or alignment guide 700, according to some embodiments. Similar to the alignment guide 602 shown in FIGS. 8A-8C, the alignment guide 700 can be used to bend or maintain the sleeve component 124 in a straight and/or selectively angled or bent configuration. Certain details or usage of the alignment guide 602 can also be implemented with the alignment guide 700, as discussed herein, and will not be repeated here for brevity.

Figure 9B:
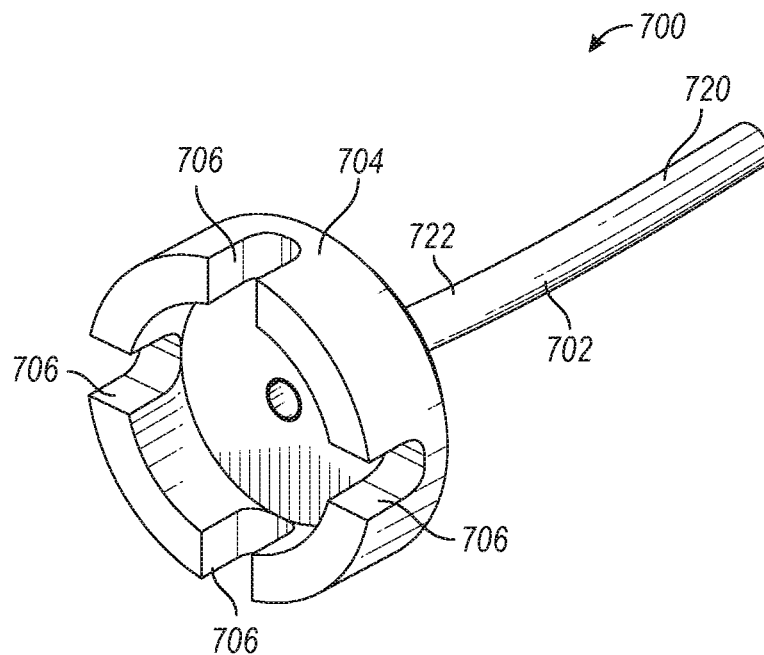
FIG. 9B is a rear perspective view of the alignment guide of FIG. 9A, according to some embodiments.

As shown in FIGS. 9A and 9B, The alignment guide 700 can comprise a guide shaft 702 that is coupled to an attachment portion 704. Similar to the alignment guide 602, the attachment portion 704 can comprise one or more index grooves 706 that facilitate alignment and/or coupling of the alignment guide 700 relative to the housing 102 of the inserter 100.

As with the alignment guide 602 discussed above, the inserter 100 can be delivered with the alignment guide 700 coupled to the inserter 100 or disposed over the sleeve component 124. In some embodiments, the hollow guide shaft 702 can be disposed over portions of the sleeve component 124 and the needle component 120. The guide shaft 702 can have an angle similar to or determine the angle of the angled sleeve component described herein. The alignment guide 700 can bend the sleeve component 124 and the needle component 120 and provide an angular deviation 710 of an axis 712 of the guide shaft 702 from a longitudinal axis 178 of the inserter 100 within a range of between about 0 degrees and about 30 degrees, between about 0 degrees and about 20 degrees, between about 0 degrees and about 15 degrees, or at about 8 degrees relative to the longitudinal axis of the inserter.

Additionally, similar to the alignment guide 602, an insertion or distal end portion 720 of the guide shaft 702 can be substantially straight while a deployment or proximal end portion 722 of the guide shaft 702 can comprise a curve or bend. Further, in some embodiments, the distal end portion 720 and the proximal end portion 722 can both comprise a bend or be straight with a bend section disposed therebetween. The proximal end portion 722 can be about one quarter to about one half of the overall length of the guide shaft 702. In some embodiments, the length of the proximal end portion 722 can be about one third of the length of the guide shaft 702. Accordingly, in some embodiments, the distal end portion 720 can be about one half to about three quarters of the length of the guide shaft 702, and in some embodiments, about two thirds of the length of the guide shaft 702.

Similar to the alignment guide 602, the alignment guide 700 can allow an operator to modify the angle of the sleeve component 124 and the needle component 120 prior to a procedure (e.g., by permitting the operator to select from a variety of different alignment guides having different angular orientations and configurations of relative lengths of the proximal and distal end portions) without having to replace the needle component 120 of the inserter 100. Further, the guide shaft 702 can provide enhanced stiffness to the sleeve component 124 and the needle component 120. In some embodiments, the alignment guide 700 can facilitate the use of thinner gauge needles for the needle component 120, including, but not limited to needles of 28 Gauge or thinner in size. Thus, implementations of the present disclosure can advantageously allow very small, delicate needles to be used in the delivery of an intraocular shunt while ensuring that the needle exhibits sufficient strength and stiffness during the delivery process.

As also similarly noted above, the sleeve component 124 and the needle component 120 can be flexible or elastic to allow deflection when the alignment guide 700 is installed. The alignment guide 700 can be removed to allow the sleeve component 124 and the underlying needle component 120 to move to a default straight configuration. For example, the alignment guide 700 can be configured to elastically deform the sleeve component 124. Thus, upon removal of the alignment guide 700, the sleeve component 124 and the needle component 120 will return to a straight configuration. Further, the alignment guide 700 can be reinstalled on the housing 102, if needed.

As noted similarly above with respect to FIGS. 8A-8C, the alignment guide 700 of FIGS. 9A and 9B can be properly rotationally aligned relative to the inserter 100 by the attachment portion 704, which can be keyed or indexed, that orients the alignment guide 700 relative to the housing 102. The index grooves 706 of the attachment portion 704 can align with the index protrusions 105 of the housing 102. In some embodiments, the index grooves 706 can be keyed to the index protrusions 105 to allow the alignment guide 700 to attach to the housing 102 in a desired orientation. Thus, the alignment guide 700 and the inserter 100 can be configured to have one or more preset relative orientations. The index grooves 706 can be in the shape of longitudinally extending indentations or slots formed in the attachment portion 704.

Further, the index grooves 706 can be spaced apart from each other (e.g., circumferentially) at equal circumferential distances, and the index protrusions 105 can be spaced apart from each other (e.g., circumferentially) at equal circumferential spacings, so that the alignment guide 700 can be rotated to one or more preset rotational orientations. However, the circumferential distances between the index grooves 706 and/or the index protrusions 105 can vary. In the embodiment illustrated in FIGS. 9A and 9B, there are four preset rotational orientations. In some embodiments, the alignment guide 700 can comprise a single index groove 706 that can be mated with a single index protrusion 105 of the housing 102 so that the alignment guide 700 has a single rotational orientation relative to the inserter 100.

The attachment portion 704 can have a number of index grooves 706 that is the same in number as the index protrusions 105. However, in some embodiments, the alignment guide 700 can comprise more index grooves 706 than there are index protrusions 105. For example, although there can be four index protrusions 105 and four index grooves 706, there can be four index protrusions 105 and eight index grooves 706, four index protrusions 105 and twelve index grooves 706, or ratios of index protrusions 105 to index grooves 706 of 1:4, 1:5, 1:6, or more.

In accordance with some embodiments, the attachment portion 704 of the alignment guide 700 can comprise one or more retention or engagement features that enable the alignment guide to snap onto or otherwise engage with corresponding engagement features of the distal end portion of the inserter 100. Such features can also be used in conjunction with the attachment portion 604 of the alignment guide 602.

In accordance with some embodiments, various components can be used to protect the needle component of the inserter. These components can be used individually or in combination with each other to reposition and/or protect the needle component, such as the bevel of the needle component, from being damaged during transport or shipping of the inserter or the needle assembly. Such components that can be used for this purpose include the alignment guide 602 or 700, a protective cap, and a bevel protection device. These components and examples of their combined uses are discussed below with regard to FIGS. 10A and 10B.

Figure 10A:
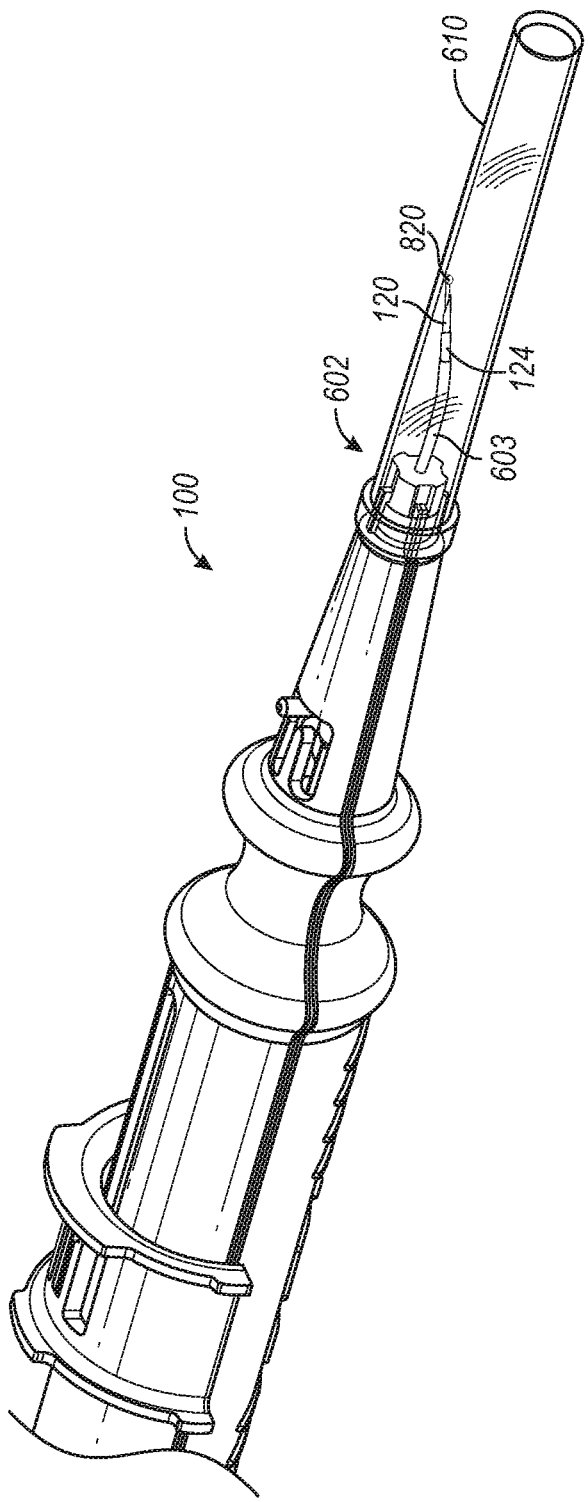
FIG. 10A is a perspective view of an alignment guide coupled to a sleeve with a protective cap, according to some embodiments.
Figure 10B:
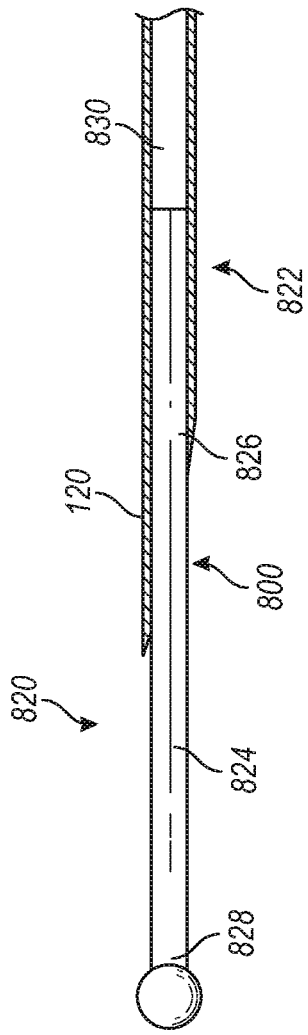
FIG. 10B is a side, cross-sectional view of a bevel protection device received within a needle lumen of an inserter, according to some embodiments.

As shown in FIGS. 10A and 10B, in some embodiments, a bevel protection device 820 can be inserted into the needle component 120 in order to protect a bevel area or bevel 800 of the needle component 120. As illustrated in FIG. 10A, in some embodiments, the alignment guide 602 (which can also be the alignment guide 700) can be coupled to the inserter 100 and used to angle the sleeve component 124 and/or needle component 120 to protect the sleeve component 124 and/or needle component 120 by keeping the sleeve component 124 angled towards the protective cap 610 while the bevel protection device 820 is inserted into the needle component 120. Thus, as illustrated, the bevel protection device 820 can extend distally from the needle component 120 and contact the inner sidewall of the protective cap 610. Therefore, with the alignment guide 602 bending the needle component 120 in a direction away from the central axis of the protective cap 610 (or toward a sidewall of the protective cap 610), the bevel protection device 820 can be configured to contact the sidewall of the protective cap 610, thus spacing the bevel 800 of the needle component 120 away from and avoiding contact with the sidewall of the protective cap 610.

Additionally, the protective cap 610 configured to engage with a portion of the housing 102 in order to secure the protective cap 610 onto a distal portion of the housing 102 in order to cover and protect the sleeve component 124 and the needle component 120.

As noted above, in accordance with some embodiments, the bevel protection device 820 can also be used to reduce or prevent inadvertent contact of the bevel 800 of the needle component with other structures, such as the protective cap 610, during transport and shipping of the inserter or the needle assembly. When used in combination with the alignment guide 602 or 700, the alignment guide 602 or 700 can cause a desired contact between the bevel protection device 820 and the protective cap 610 to position the needle component 120 in a protected position. However, in some embodiments, the bevel protection device 820 can be used with by itself or with either or both of the protective cap 610 or the alignment guide 602 or 700.

The inserter 100 can be used in combination with a bevel protection device that engages with a needle component 120 of the inserter 100 in order to prevent accidental damage to the bevel 800 of the needle component 120. In some embodiments, the bevel protection device described herein can be used with the angled sleeve component 124 and/or the alignment guide 602 or 700 to dispose an end of the protection device against the protective cap 610.

For example, FIG. 10B illustrates a distal end portion of a needle component 120 of an inserter. The bevel protection device 820 can engage with a distal end portion 822 of the needle component 120. The bevel protection device 820 can comprise an elongate body 824 that comprises a first portion 826 and a second portion 828. The first portion 826 can taper from a larger diameter cross-section to a smaller diameter cross-section. The smaller diameter cross-section can be less than an inner diameter of the distal end portion 822 of the needle component 120. Thus, the first portion 826 can be inserted into a lumen 830 of the needle component 120.

The elongate body 824 can be configured such that the tapering of the first portion 826 provides the elongate body 824 with a variable diameter cross-section. The diameter can taper gradually or in steps.

As shown in the embodiment illustrated in FIG. 10B, the cross-sectional profile or diameter of the elongate body 824 adjacent to the second portion 828 can be greater than the cross-sectional profile or diameter of the elongate body 824 near the first portion 826. For example, from the first portion 826 toward the second portion 828, the cross-sectional diameter of the elongate body 824 can increase from a diameter that is less than an inner diameter of the lumen 830 of the needle component 120 to a diameter that is greater than the inner diameter of the lumen 830. Thus, the elongate body 824 can be inserted into the lumen 830 of the needle component 120 and advanced to a position at which the cross-section of the elongate body is about equal to the inner diameter of the lumen 830, thus restricting further advancement of the bevel protection device 820 into the lumen 830.

In some embodiments, the elongate body 824 can frictionally engage with the distal end portion 822 of the needle component 120. For example, the retention device 820 can be force fit into the needle component 120 to create a frictional engagement between the outer surface of the elongate body 824 and an inner surface of the lumen 830. This frictional engagement can be overcome by exerting a withdrawal force on the second portion 828 of the retention device 820, thereby pulling the bevel protection device 820 out of the lumen 830.

Although the bevel protection device 820 is illustrated as having a circular or diametrical cross section, other cross sections can also be used, such as triangular, square, rectangular, polygonal, star-shaped, or other similar profiles. Further, the bevel protection device 820 can be made of steel. In accordance with some embodiments, the bevel protection device 820 may only contact the inside of the needle bevel 800, and therefore advantageously does not affect the needle sharpness, which is driven by the needle outside edges.

The bevel protection device 820 can therefore ensure that the edges of the bevel 800 of the needle to not come into contact with other surfaces to prevent damage during shipment or initial handling of the inserter or needle assembly. When the operator is prepared to use in inserter, the bevel protection device 820 can be withdrawn from the needle component 120 and the procedure can be carried out.

Further, in some embodiments, the inserter 100 can comprise tactile or audible feedback mechanisms that do not require or generate consistent or persistent frictional engagement against the housing 102. Thus, features of the inserter discussed herein can be incorporated into some embodiments while excluding other features discussed herein.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed within the scope of the disclosure.

Illustration of Subject Technology as Clauses

Various examples of aspects of the disclosure are described below as clauses for convenience. These are provided as examples, and do not limit the subject technology.

Clause 1. An intraocular shunt inserter for treating glaucoma, comprising: a housing having a distal portion, a proximal portion, a longitudinal axis extending between the distal and proximal portions, the housing further comprising an inner cavity, a guide channel and an elongate slot, the guide channel extending along the longitudinal axis and accessible along an outer surface of the housing, the guide channel having an inner wall, the elongate slot extending along the longitudinal axis along the outer surface of the housing into the inner cavity; and a slider component slidably coupled to the housing along the outer surface thereof, the slider component slidable along the elongate slot for actuating a function of the inserter via the elongate slot, the slider component comprising a guide tab and a friction tab, the guide tab disposed within and slidable along the guide channel of the housing, the friction tab being movable relative to the guide tab and comprising a biasing portion configured to urge the friction tab against the housing for causing the guide tab to be contacted against the inner wall of the guide channel for providing frictional resistance between the slider component and the housing against sliding.

Clause 2. The inserter of Clause 1, wherein the slider component comprises an interior region into which the housing is fitted.

Clause 3. The inserter of Clause 2, wherein the interior region is semi-cylindrical.

Clause 4. The inserter of any of Clauses 2 to 3, wherein the friction tab extends inwardly toward the interior region of the slider component for contacting an outer surface of the housing.

Clause 5. The inserter of Clause 4, wherein the friction tab comprises a pair of friction tabs extending inwardly toward the interior region of the slider component.

Clause 6. The inserter of any of Clauses 2 to 5, wherein the guide tab extends inwardly toward the interior region of the slider component.

Clause 7. The inserter of any of Clauses 2 to 6, wherein the guide tab comprises a pair of guide tabs extending inwardly toward the interior region of the slider component.

Clause 8. The inserter of any of Clauses 2 to 8, wherein the slider component comprises a generally cylindrical profile and the guide tabs are spaced between about 90 degrees to about 180 degrees apart from each other along an inner surface of the interior region.

Clause 9. The inserter of any of the preceding Clauses, wherein when coupled to the housing, the slider component contacts the housing only via the guide tab and the friction tab.

Clause 10. The inserter of any of the preceding Clauses, wherein the guide tab comprises a pair of guide tabs, each of the pair of guide tabs comprising a longitudinally extending flange configured to sit within the guide channel.

Clause 11. The inserter of any of the preceding Clauses, wherein the housing comprises a generally cylindrical profile and a pair of guide channels are spaced between about 90 degrees to about 180 degrees apart from each other along the outer surface of the housing.

Clause 12. The inserter of Clause 11, wherein the guide channels are disposed about 180 degrees from each other.

Clause 13. The inserter of any of the preceding Clauses, wherein the guide tab, the friction tab, and the slider component are formed as a single, continuous piece of material.

Clause 14. The inserter of any of the preceding Clauses, wherein the friction tab is formed as a cut out through a body of the slider component.

Clause 15. The inserter of Clause 14, wherein the friction tab comprises a protrusion extending toward an interior region of the slider component.

Clause 16. The inserter of Clause 15, wherein when the slider component is coupled to the housing, the protrusion of the friction tab contacts the housing.

Clause 17. The inserter of Clause 16, wherein the protrusion of the friction tab contacts the housing to cause the friction tab to bend in a direction away from the guide tab.

Clause 18. The inserter of any of the preceding Clauses, wherein the housing comprises a generally cylindrical profile.

Clause 19. The inserter of any of the preceding Clauses, wherein the housing comprises an engagement structure against which the friction tab can contact the housing for providing audible or tactile feedback to an operator.

Clause 20. The inserter of Clause 19, wherein the engagement structure comprises at least one discontinuity in the outer surface of the housing.

Clause 21. The inserter of Clause 19, wherein the engagement structure comprises at least one bump on the outer surface of the housing.

Clause 22. The inserter of Clause 19, wherein the engagement structure comprises a plurality of serrated features on the outer surface of the housing.

Clause 23. The inserter of Clause 19, wherein the engagement structure comprises a plurality of tapered peaks on the outer surface of the housing.

Clause 24. The inserter of Clause 19, wherein the function of the inserter comprises advancing a shunt within a needle, and a position of the slider component along the engagement structure corresponds to a deployment position of the shunt relative to the needle.

Clause 25. The inserter of Clause 19, wherein the engagement structure comprises a plurality of bumps on the outer surface of the housing, wherein each of the bumps corresponds to a deployment position of an intraocular shunt.

Clause 26. The inserter of any of the preceding Clauses, wherein the slider component is operatively coupled to a deployment mechanism within the housing.

Clause 27. The inserter of Clause 26, wherein the slider component is coupled to the deployment mechanism via a rod extending through the elongate slot, the rod being coupled to the slider component and the deployment mechanism.

Clause 28. The inserter of any of the preceding Clauses, further comprising a hollow needle that comprises a bend at an angle of between about 6 degrees to about 10 degrees, the needle being configured to carry an intraocular shunt.

Clause 29. The inserter of Clause 28, wherein the needle defines a straight section and an angled section.

Clause 30. The inserter of any of the preceding Clauses, further comprising a hollow needle extending from a distal end portion of the inserter, the inserter further comprising a deflector component releasably attachable to the distal end portion of the inserter, and wherein when the deflector component is coupled to the inserter, the hollow needle extends through the deflector component and the deflector maintains the needle in a bended configuration.

Clause 31. The inserter of Clause 30, wherein in the bended configuration, the needle is bended at an angle of between about 6 degrees to about 10 degrees.

Clause 32. The inserter of Clause 30, wherein when coupled with the deflector, the needle is elastically deformed.

Clause 33. The inserter of Clause 30, wherein the distal end portion of the inserter comprises an indexing structure and the deflector component comprises an alignment index, wherein the alignment index of the deflector component can be releasably engaged with the indexing structure to define a rotational orientation of the deflector component relative to the inserter.

Clause 34. The inserter of Clause 33, wherein the deflector component comprises a bent needle guide attached to and extending from a coupler, wherein the alignment index is formed along the coupler.

Clause 35. The inserter of Clause 34, wherein the alignment index is positioned along a proximal portion of the coupler.

Clause 36. The inserter of Clause 34, wherein the alignment index comprises at least one groove extending along a perimeter of the coupler.

Clause 37. The inserter of Clause 34, wherein the needle guide comprises a hollow shaft.

Clause 38. The inserter of Clause 33, wherein the indexing structure comprises at least one protrusion configured to slide into a corresponding groove.

Clause 39. An intraocular shunt inserter for treating glaucoma, comprising: a housing having a distal portion, a proximal portion, and a longitudinal axis extending between the distal and proximal portions, the housing further comprising an interior cavity, a guide channel, and an elongate slot extending along an outer surface of the housing into the cavity for actuating a function of the inserter; and a slider component coupled to the housing and positioned along the outer surface thereof, the slider component slidable along the elongate slot, the slider comprising a guide tab disposed within the guide channel; and a position feedback mechanism comprising a biased tab and an engagement structure, the biased tab being coupled to the slider component, the engagement structure being formed along the outer surface of the housing, wherein motion of the slider component causes the biased tab to slide along the engagement structure to generate tactile or audible feedback to an operator regarding a position of an intraocular shunt relative to the inserter.

Clause 40. The inserter of Clause 39, wherein the engagement structure comprises at least one discontinuity in the outer surface of the housing.

Clause 41. The inserter of any of Clauses 39 to 40, wherein the engagement structure comprises at least one bump on the outer surface of the housing.

Clause 42. The inserter of any of Clauses 39 to 41, wherein the engagement structure comprises a plurality of serrated features on the outer surface of the housing.

Clause 43. The inserter of any of Clauses 39 to 42, wherein the engagement structure comprises a plurality of tapered peaks on the outer surface of the housing.

Clause 44. The inserter of any of Clauses 39 to 43, wherein the function of the inserter comprises advancing a shunt within a needle, and a position of the slider component along the engagement structure corresponds to a deployment position of the shunt relative to the needle.

Clause 45. The inserter of any of Clauses 39 to 44, wherein the engagement structure comprises a plurality of bumps on the outer surface of the housing, wherein each of the bumps corresponds to a deployment position of an intraocular shunt.

Clause 46. The inserter of Clause 45, wherein each of the plurality of bumps is disposed along the housing at positions corresponding to rotational positions of a drive component of a deployment mechanism of the inserter.

Clause 47. The inserter of any of Clauses 39 to 46, further comprising a hollow needle extending from a distal end portion of the inserter, the inserter further comprising a deflector component releasably attachable to the distal end portion of the inserter, and wherein when the deflector component is coupled to the inserter, the hollow needle extends through the deflector component and the deflector maintains the needle in a bended configuration.

Clause 48. The inserter of Clause 47, wherein in the bended configuration, the needle is bended at an angle of between about 6 degrees to about 10 degrees.

Clause 49. The inserter of Clause 47, wherein when coupled with the deflector, the needle is elastically deformed.

Clause 50. The inserter of Clause 52, wherein the needle guide comprises a hollow shaft.

Clause 51. The inserter of Clause 47, wherein the distal end portion of the inserter comprises an indexing structure and the deflector component comprises an alignment index, wherein the alignment index of the deflector component can be releasably engaged with the indexing structure to define a rotational orientation of the deflector component relative to the inserter.

Clause 52. The inserter of Clause 51, wherein the deflector component comprises a bent needle guide attached to and extending from a coupler, wherein the alignment index is formed along the coupler.

Clause 53. The inserter of Clause 52, wherein the alignment index is positioned along a proximal portion of the coupler.

Clause 54. The inserter of Clause 52, wherein the alignment index comprises at least one groove extending along a perimeter of the coupler.

Clause 55. The inserter of Clause 54, wherein the indexing structure comprises at least one protrusion configured to slide into the at least one groove.

Clause 56. The inserter of Clause 47, wherein the needle is elastically deformable.

Clause 57. A method of operating an intraocular shunt inserter, the method comprising: distally advancing a slider component along a housing of an intraocular shunt inserter by overcoming a frictional resistance between a friction tab of the slider component and the housing, the slider component being slidable for actuating a function of the inserter, the slider component comprising a guide tab and a friction tab, the guide tab disposed within and slidable along a guide channel of the housing, the friction tab being movable relative to the guide tab and comprising a biasing portion configured to urge the friction tab against the housing for causing the guide tab to be contacted against an inner wall of the guide channel for providing the frictional resistance between the slider component and the housing; and contacting a plunger, engaged with the slider, against a shunt disposed within a needle of the inserter to distally advance the shunt within the needle.

Clause 58. The method of Clause 57, further comprising engaging a discontinuity of the housing via the friction tab.

Clause 59. The method of Clause 58, further comprising generating an audible signal by engaging the discontinuity.

Clause 60. The method of any of Clauses 58 to 59, wherein a position of the discontinuity corresponds to a position of the shunt within a lumen of the needle.

Clause 61. The method of Clause 60, wherein the discontinuity comprises a bump.

Clause 62. The method of Clause 60, wherein the discontinuity comprises a serrated feature.

Clause 63. The method of Clause 60, wherein the discontinuity comprises a tapered peak.

Clause 64. The method of any of Clauses 57 to 63, further comprising bending the needle of the inserter by coupling a deflector component to a distal end portion of the inserter.

Clause 65. The method of Clause 64, wherein the bending comprises inserting the needle through the deflector component to cause the needle to bend.

Clause 66. The method of Clause 64, wherein the bending comprises bending the needle at an angle of between about 6 degrees to about 10 degrees.

Clause 67. The method of Clause 64, wherein the deflector component defines a straight insertion portion and an angled deployment portion.

Clause 68. The method of Clause 64, further comprising aligning the deflector component with the distal end portion of the inserter via an indexing mechanism.

Clause 69. The method of Clause 68, wherein the indexing mechanism comprises at least one protrusion on the distal end portion of the inserter.

Clause 70. The method of any of Clauses 57 to 69, further comprising elastically deforming the needle.

Clause 71. A system for deploying an intraocular shunt, the system comprising: an intraocular shunt inserter comprising a housing having a distal end portion and a needle extending from the distal end portion; and a deflector component releasably attachable to the distal end portion of the inserter, the deflector component having a needle guide configured to receive the needle of the inserter therein, wherein the needle guide maintains the needle in a bended configuration.

Clause 72. The system of Clause 71, wherein the needle guide comprises a hollow shaft.

Clause 73. The system of any of Clauses 71 to 72, wherein in the bended configuration, the needle is bended at an angle of between about 6 degrees to about 10 degrees.

Clause 74. The system of any of Clauses 71 to 73, wherein when coupled with the deflector component, the needle is elastically deformed.

Clause 75. The system of any of Clauses 71 to 74, wherein the distal end portion of the inserter comprises an indexing structure and the deflector component comprises an alignment index, wherein the alignment index of the deflector component can be releasably engaged with the indexing structure to define a rotational orientation of the deflector component relative to the inserter.

Clause 76. The system of Clause 75, wherein the deflector component comprises a coupler, the needle guide being attached to the coupler, wherein the alignment index is formed along the coupler.

Clause 77. The system of Clause 76, wherein the alignment index is positioned along a proximal portion of the coupler.

Clause 78. The system of Clause 76, wherein the alignment index comprises at least one groove extending along a perimeter of the coupler.

Clause 79. The system of Clause 76, wherein the indexing structure comprises at least one protrusion configured to slide into a corresponding groove.

Clause 80. An intraocular shunt delivery device, comprising: a cylindrical housing comprising guide channels extending longitudinally along the housing, each guide channel defining an inner wall having an upper face; and a semi-cylindrical slider disposed about the housing, wherein the slider is axially moveable relative to the housing, the slider comprising: a pair of guide tabs disposed within respective ones of the guide channels of the housing to secure the slider to the housing; a friction tab, disposed intermediate the guide tabs on the slider, comprising a biasing portion configured to urge the friction tab against the housing for causing the guide tab to be contacted against the inner wall of the guide channel; and a slider protrusion operatively coupled to a shunt deployment mechanism within the housing.

Clause 81. The delivery device of Clause 80, wherein the guide channels are disposed about 180 degrees from each other.

Clause 82. The delivery device of any of Clauses 80 to 81, wherein the slider protrusion passes through the housing to the deployment mechanism.

Clause 83. The delivery device of any of Clauses 80 to 82, wherein the housing comprises an engagement structure disposed along an outer surface of the housing against which the friction tab can contact the housing for providing audible or tactile feedback to an operator.

Clause 84. The delivery device of Clause 83, wherein the engagement structure comprises a groove, an indentation, or a protrusion.

Clause 85. The delivery device of Clause 83, wherein the engagement structure comprises at least one discontinuity to receive the biasing portion.

Clause 86. The delivery device of Clause 83, wherein the engagement structure comprises at least one bump on the outer surface of the housing.

Clause 87. The delivery device of Clause 83, wherein the engagement structure comprises a plurality of serrated features on the outer surface of the housing.

Clause 88. The delivery device of Clause 83, wherein the engagement structure comprises a plurality of tapered peaks on the outer surface of the housing.

Clause 89. The delivery device of any of Clauses 80 to 88, further comprising a hollow needle that comprises a bend at an angle of between about 6 degrees to about 10 degrees and is configured to hold an intraocular shunt.

Clause 90. The delivery device of Clause 89, wherein the bend defines a straight insertion portion and an angled deployment portion of the needle.

Clause 91. The delivery device of Clause 89, further comprising a deflector component releasably attachable to a distal end portion of the delivery device, and wherein when the deflector component is coupled to the delivery device, the hollow needle extends through the deflector component and the deflector maintains the needle in a bended configuration.

Clause 92. The delivery device of Clause 91, wherein the needle is elastically deformed.

Clause 93. The delivery device of Clause 91, wherein the distal end portion of the delivery device comprises an indexing structure and the deflector component comprises an alignment index, wherein the alignment index of the deflector component can be releasably engaged with the indexing structure to define a rotational orientation of the deflector component relative to the delivery device.

Clause 94. An inserter device for deploying an intraocular shunt, the device comprising: a housing; a shunt deployment mechanism disposed within the housing; a deformable hollow needle coupled to the housing and the deployment mechanism for delivering an intraocular shunt; and a deflector component releasably attachable to a distal end portion of the housing, the deflector component comprising a coupling body and a needle guide positionable against a portion of the needle to cause the needle to be positioned in a bended configuration.

Clause 95. The device of Clause 94, wherein the needle guide comprises a bend at an angle of between about 0 degrees to about 15 degrees.

Clause 96. The device of any of Clauses 94 to 95, wherein the needle guide comprises a bend at an angle of between about 2 degrees to about 10 degrees.

Clause 97. The device of any of Clauses 94 to 96, wherein the needle guide comprises a bend at an angle of between about 3 degrees to about 8 degrees.

Clause 98. The device of any of Clauses 94 to 97, wherein the needle guide comprises a bend at an angle of between about 4 degrees to about 6 degrees.

Clause 99. The device of any of Clauses 94 to 98, wherein the needle guide comprises a straight insertion portion and an angled deployment portion.

Clause 100. The device of any of Clauses 94 to 99, wherein the needle is elastically deformable.

Clause 101. The device of any of Clauses 94 to 100, wherein the housing comprises an indexing structure and the deflector component comprises an alignment index, wherein the alignment index of the deflector component can be releasably engaged with the indexing structure to define a rotational orientation of the deflector component relative to the inserter device.

Clause 102. The device of Clause 101, wherein the indexing structure comprises a plurality of index grooves.

Clause 103. The device of Clause 102, wherein the plurality of index grooves are configured to receive a plurality of index protrusions of the deflector component.

Clause 104. The device of Clause 101, wherein the indexing structure defines a plurality of orientations at which the deflector component can engage with the housing.

Clause 105. The device of any of Clauses 94 to 104, further comprising a slider component as recited in any of the preceding Clauses.

Clause 106. A method of operating an intraocular shunt inserter, the method comprising: providing an inserter device for deploying an intraocular shunt, the device comprising a housing having a distal end portion, a shunt deployment mechanism disposed within the housing, and a deformable hollow needle coupled to the housing and the deployment mechanism for delivering an intraocular shunt; inserting the needle into a needle guide of a deflector component to cause the needle to be positioned in a bended configuration; and coupling the deflector component to the distal end portion of the housing with a coupling body of the deflector component positioned against the distal end portion.

Clause 107. The method of Clause 106, wherein the inserting comprising causing the needle to be bended at an angle of between about 0 degrees to about 15 degrees in the bended configuration.

Clause 108. The method of any of Clauses 106 to 107, wherein the inserting comprising causing the needle to be bended at an angle of between about 6 degrees to about 10 degrees in the bended configuration.

Clause 109. The method of any of Clauses 106 to 108, wherein the inserting comprising causing the needle to be bended at an angle of between about 2 degrees to about 10 degrees in the bended configuration.

Clause 110. The method of any of Clauses 106 to 109, wherein the inserting comprising causing the needle to be bended at an angle of between about 3 degrees to about 8 degrees in the bended configuration.

Clause 111. The method of any of Clauses 106 to 110, wherein the inserting comprising causing the needle to be bended at an angle of between about 4 degrees to about 6 degrees in the bended configuration.

Clause 112. The method of any of Clauses 106 to 111, wherein the needle guide comprises a straight insertion portion and an angled deployment portion.

Clause 113. The method of any of Clauses 106 to 112, further comprising aligning the deflector component with the distal end portion of the inserter via an indexing mechanism.

Clause 114. The method of Clause 113, wherein the indexing mechanism comprises at least one protrusion on the distal end portion of the inserter.

Clause 115. The method of any of Clauses 113 to 114, wherein the aligning comprises rotationally aligning the deflector component relative to the housing.

Clause 116. The method of Clause 115, wherein the rotationally aligning comprises selecting an indexed rotational position from a plurality of rotational positions.

Clause 117. A device incorporating any of the features recited in any of the preceding Clauses.

Clause 118. A method incorporating any of the features recited in any of the preceding Clauses.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. An intraocular shunt inserter for treating glaucoma, comprising:

a housing having a distal portion, a proximal portion, a longitudinal axis extending between the distal and proximal portions, the housing further comprising an inner cavity, a guide channel, an elongate slot, and an indicator area, the guide channel extending along the longitudinal axis and accessible along an outer surface of the housing, the guide channel having an inner wall, the elongate slot extending along the longitudinal axis along the outer surface of the housing into the inner cavity, wherein the indicator area comprises a first plurality of discontinuities grouped together and a second plurality of discontinuities grouped together and spaced apart from the first plurality of discontinuities; and a slider component slidably coupled to the housing along the outer surface thereof, the slider component slidable along the elongate slot for actuating a function of the inserter to cause deployment of the intraocular shunt via the elongate slot, the slider component comprising a guide tab and a friction tab, the guide tab disposed within and slidable along the guide channel of the housing, the friction tab being movable relative to the guide tab and comprising a biasing portion configured to urge the friction tab against the housing for causing the friction tab to contact the indicator area to provide audible or tactile feedback to an operator.

2. The inserter of claim 1, wherein the slider component comprises an interior region into which the housing is fitted.

3. The inserter of claim 2, wherein the friction tab extends inwardly toward the interior region of the slider component for contacting an outer surface of the housing.

4. The inserter of claim 2, wherein the guide tab extends inwardly toward the interior region of the slider component.

5. The inserter of claim 2, wherein the slider component comprises a generally cylindrical profile and the guide tab are spaced between about 90 degrees to about 180 degrees apart from each other along the interior region.

6. The inserter of claim 1, wherein the housing comprises a generally cylindrical profile and a pair of guide channels are spaced between about 90 degrees to about 180 degrees apart from each other along the outer surface of the housing.

7. The inserter of claim 1, wherein the friction tab is formed as a cut out through a body of the slider component.

8. The inserter of claim 1, wherein at least one discontinuity of the first plurality of discontinuities comprises at least one bump on the outer surface of the housing.

9. The inserter of claim 1, wherein the slider component is operatively coupled to a deployment mechanism within the housing.

10. The inserter of claim 1, wherein the first plurality of discontinuities and the second plurality of discontinuities each corresponds to a different deployment position of an intraocular shunt.

11. The inserter of claim 1, wherein the housing between the first plurality of discontinuities and the second plurality of discontinuities comprises a generally cylindrical profile free of discontinuities preventing the friction tab from providing audible or tactile feedback to the operator between the first plurality of discontinuities and the second plurality of discontinuities.

12. The inserter of claim 1, wherein the first plurality of discontinuities is spaced apart from the second plurality of discontinuities by at least about a longitudinal extent of the first plurality of discontinuities or the second plurality of discontinuities.

13. An intraocular shunt inserter for treating glaucoma, comprising:

a housing having a distal portion, a proximal portion, and a longitudinal axis extending between the distal and proximal portions, the housing further comprising an interior cavity, a guide channel, and an elongate slot extending along an outer surface of the housing into the cavity for actuating a function of the inserter to cause deployment of an intraocular shunt;

a slider component coupled to the housing and positioned along the outer surface thereof, the slider component slidable along the elongate slot, the slider comprising a guide tab disposed within the guide channel; and a position feedback mechanism comprising a biased tab and an indicator area, the biased tab being coupled to the slider component, the indicator area being formed along the outer surface of the housing, wherein motion of the slider component causes the biased tab to slide along the indicator area to generate tactile or auditory feedback to an operator regarding a position of an intraocular shunt relative to the inserter, wherein the indicator area comprises a first plurality of discontinuities grouped together and a second plurality of discontinuities grouped together and spaced apart from the first plurality of discontinuities.

14. The inserter of claim 13, wherein at least one discontinuity of the first plurality of discontinuities comprises at least one bump on the outer surface of the housing.

15. The inserter of claim 13, wherein each of the first plurality of discontinuities is disposed along the housing at positions corresponding to rotational positions of a drive component of a deployment mechanism of the inserter.

16. The inserter of claim 13, wherein the first plurality of discontinuities and the second plurality of discontinuities each corresponds to a different deployment position of the intraocular shunt.

17. The inserter of claim 13, wherein the housing between the first plurality of discontinuities and the second plurality of discontinuities comprises a generally cylindrical profile free of discontinuities preventing the biased tab from generating tactile or auditory feedback to the operator between the first plurality of discontinuities and the second plurality of discontinuities.

18. The inserter of claim 13, wherein the first plurality of discontinuities is spaced apart from the second plurality of discontinuities by at least about a longitudinal extent of the first plurality of discontinuities or the second plurality of discontinuities.

19. A method of operating an intraocular shunt inserter, the method comprising:

distally advancing a slider component along a housing of an intraocular shunt inserter, the slider component being slidable for actuating a function of the inserter to cause deployment of an intraocular shunt, the slider component comprising a guide tab and a friction tab, the guide tab disposed within and slidable along a guide channel of the housing, the friction tab being movable relative to the guide tab and comprising a biasing portion configured to urge the friction tab against the housing for causing the guide tab to be contacted against an inner wall of the guide channel;

engaging at least a portion of an indicator area of the housing via the friction tab, wherein the indicator area comprises a first plurality of discontinuities grouped together and a second plurality of discontinuities grouped together and spaced apart from the first plurality of discontinuities; and contacting a plunger, engaged with the slider, against the shunt disposed within a needle of the inserter to distally advance the shunt within the needle.

20. The method of claim 19, further comprising generating an auditory signal by engaging at least one discontinuity of the first plurality of discontinuities.

21. The method of claim 20, further comprising preventing generation of the auditory signal between the first plurality of discontinuities and the second plurality of discontinuities.

22. The method of claim 19, wherein a position of at least one discontinuity of the first plurality of discontinuities corresponds to a position of the shunt within a lumen of the needle.

23. The method of claim 22, wherein at least one discontinuity of the first plurality of discontinuities comprises a bump.

24. The method of claim 19, wherein the first plurality of discontinuities and the second plurality of discontinuities each corresponds to a different deployment position of the intraocular shunt.

25. The method of claim 19, wherein the first plurality of discontinuities is spaced apart from the second plurality of discontinuities by at least about a longitudinal extent of the first plurality of discontinuities or the second plurality of discontinuities.

* * * * *